US007087552B2

(12) United States Patent
Blowers et al.

(10) Patent No.: US 7,087,552 B2
(45) Date of Patent: *Aug. 8, 2006

(54) MODIFICATION OF FLORAL SCENT IN FLOWERING PLANTS

(75) Inventors: Alan Blowers, St. Charles, IL (US); Natalia Dudareva, Lafayette, IN (US)

(73) Assignees: Ball Horticultural Company, West Chicago, IL (US); Purdue Research Foundation, West Lafayette, IN (US)

( * ) Notice: Subject to any disclaimer, the term of this patent is extended or adjusted under 35 U.S.C. 154(b) by 281 days.

This patent is subject to a terminal disclaimer.

(21) Appl. No.: 10/210,363

(22) Filed: Aug. 1, 2002

(65) Prior Publication Data

US 2003/0078165 A1 Apr. 24, 2003

Related U.S. Application Data

(63) Continuation of application No. 09/733,840, filed on Dec. 8, 2000, now abandoned.

(60) Provisional application No. 60/170,237, filed on Dec. 10, 1999.

(51) Int. Cl.
*A01N 3/02* (2006.01)
*A01P 21/00* (2006.01)

(52) U.S. Cl. .................... 504/114; 504/115; 504/194; 504/320; 504/321; 504/324; 504/348; 504/354

(58) Field of Classification Search ............. 504/114, 504/115, 320, 321, 324, 348, 354, 194
See application file for complete search history.

(56) References Cited

U.S. PATENT DOCUMENTS

| 4,827,663 | A | * | 5/1989 | Stern |
|---|---|---|---|---|
| 5,353,546 | A | | 10/1994 | Bock |
| 5,477,640 | A | | 12/1995 | Holtkamp, Jr. |
| 5,635,443 | A | | 6/1997 | Lesenko ............... 504/114 |
| 6,013,524 | A | | 1/2000 | Friars et al. |
| 6,558,922 | B1 | * | 5/2003 | Doudareva et al. ........ 435/69.1 |

FOREIGN PATENT DOCUMENTS

| GB | 2189676 | 4/1986 |
|---|---|---|
| WO | WO 00/50613 | 8/2000 |

OTHER PUBLICATIONS

Ahmad et al., Acta Hortic. (1998), 454(Third International Symposium on New Floricultural Crops, 1996), 355-363.*
Jakobsen et al., Planta, 1994, vol. 192, No. 3, p. 365-371.
Planta, 1994. vol. 192, No. 3., 365-371.*
Ohyama et al. Soil Sci Plant Nutr, (1988) 34 (3), 405-416.*
Lichtenthaler et al., *Physiologia Plantarum*, 101:643-652 (1997).
Krundsen et al., *Phytochemistry*, 33(2):253-280 (1993).
Shulaev et al., *Nature*, 385:718-721 (1997).
McCaskill et al., *Tibtech*, 16:349-355 (1998).
McGarvey et al., *The Plant Cell*, 7:1015-1026 (1995).
Dudareva et al., *The Plant Cell*, 8:1137-1148 (1996).
Wang et al., *Plant Physiol.*, 114:213-221 (1997).
Dudareva et al., *The Plant Journal*, 14(3):297-304 (1998).
Dudareva et al., *Plant Physiol.*, 116:599-604 (1998).
Wang et al., *Archives of Biochemistry and Biiophysics*, 349(1):153-160 (1998).
Ross et al., *Archives of Biochemistry and Biophysics*, 367(1):9-16(1999).
Duareva et al., *Plant Physiology*, 122:627-633 (2000).
Bushue et al., *Plant Biology*, p. 80, PlantBiology '99, American Society of Plant Physiologists, Balitmore, Maryland U.S.A. (Jul. 1999).
PCT Search Report For PCT/US00/33392 (Mar. 19, 2001).
PCT International Preliminary Examination Report for PCT/US00/33392 (Dec. 12, 2001).
Not Making Scents www.sciam.com (1999).
Official Communication EP00984102.4-2110 (Apr. 1, 2003).
Written Opinion for PCT/US00/33392 (Aug. 17, 2001).
Amiot et al., Apidologie, 20(2): 115-125 (1989).
Anne, O., Flavor and Fragrance Journal, 1:115-119 (1986).

(Continued)

Primary Examiner—S. Mark Clardy
(74) Attorney, Agent, or Firm—Wood, Phillips, Katz, Clark & Mortimer

(57) ABSTRACT

The present invention relates to methods for creating, manipulating, modifying and enhancing floral scent component to plants and cut flowers.

57 Claims, No Drawings

OTHER PUBLICATIONS

Blum et al., Journal of Chemical Ecology, 19(12):2791-2811 (1993).
Cseke et al., Mol. Biol. Evol., 15(11):1491-1498 (1998).
Hirai, et al., Plant Cell Physiol., 36(2):291-297 (1995).
Hohn et al., Plant Physiol., 97:460-462 (1991).
Jay et al., Biochem.Physiol. Pflanzen, 181:199-206 (1986).
Kaiser et al., Tetrahedron Letters, 38:3413-3416 (1974).
Ram et al., Journal of Medicinal and Aromatic Plant Sciences 19:24-27 (1997).
Yalovsky, et al., Plant Physiol., 110:1349-1359 (1996).

* cited by examiner

US 7,087,552 B2

MODIFICATION OF FLORAL SCENT IN FLOWERING PLANTS

RELATED APPLICATION INFORMATION

This application claims priority from U.S. Application No. 60/170,237 filed on Dec. 10, 1999.

Continuation of prior application Ser. No. 09/733,840, filed Dec. 8, 2000 now abandoned.

FIELD OF THE INVENTION

The present invention relates to a composition and methods for modifying the floral scent of flowering plants and cut flowers. Additionally, the present invention can also be used to manipulate the biosynthesis and/or emission of plant-derived floral scent components. More specifically, the present invention relates to a series of methods by which chemical compositions can be introduced into flowering plants and cut flowers for the purpose of modifying the production and/or emission of volatile floral scent compounds from flowers, foliage and fruits by the application of an effective amount of at least one floral scent precursor. Additionally, the present invention further relates to methods for modifying the emission of floral scent from cut flowers which have been subjected to conditions of refrigerated temperatures and/or darkness over extended periods of time.

BACKGROUND OF THE INVENTION

The chemical composition of floral scents has been extensively investigated for hundreds of years because of the commercial value of floral volatiles in the perfumery industry. These investigations have determined that floral scents are almost always a complex mixture of small (approximately 100–250 daltons) volatile molecules and are dominated by monoterpenoid and sesquiterpenoid, phenylpropanoid, and benzenoid compounds. Fatty acid-derivatives and a range of other chemicals, especially those containing nitrogen or sulfur, are also sometimes present (for review, see Knudsen et al., 1993, *Phytochemistry* 333:253–280). However, in contrast to the chemical emphasis of the perfumers, until recently, there have been few studies concerning the biochemical synthesis of floral scent compounds and the enzymes and genes that control these processes. In fact, very recent investigations into the biogenesis of floral scent production in *Clarkia breweri*, an annual plant native to California, represents the best example to date in which isolation of enzymes and genes involved in the de novo synthesis of scent compounds in the flower have been reported.

Many plants emit floral scents, and such scents can attract a variety of animal pollinators, mostly insects. Floral scents vary widely among species in terms of the number, identity, and relative amounts of constituent volatile compounds. Plants did not naturally evolve to produce their scent for the benefit of humans; nevertheless, it is clear that humans find an aesthetic value in certain types of floral scents, and the presence of floral scent may have contributed to the decision by humans to cultivate and propagate specific plant species. While there is certainly a wide variation in human preference, most people prefer the scents of bee-pollinated and, especially, moth-pollinated flowers, which they often describe as "sweet-smelling". Some volatile compounds found in floral scent have important functions in vegetative processes as well. They may function as attractants for the natural predators of herbivores or as airborne signals that activate disease resistance via the expression of defense-related genes in neighboring plants and in the healthy tissues of infected plants (Shulaev et al., 1997, *Nature* 385:718–721). They may also serve as repellents against herbivores (Gershenzon and Croteau, 1991, in Rosenthal, G. A. and Berenbaum, M. R., eds., *Herbivores: Their Interactions with Secondary Plant Metabolites*, 168–220). However, it cannot be taken for granted that the biosynthesis of such compounds in vegetative tissue will in all cases be identical (i.e., same reactions, same enzymes) to their synthesis in flowers.

Ornamental plants are valued for their visual attributes such as flower color and architecture, and plant habit. However, their non-visual benefits are also be deemed to be quite commercially valuable since these features might include unusual textures, but especially the fragrant volatiles emitted by both flower petals and foliage. Unfortunately, very few plants are currently cultivated primarily for their scent. It is a commonly-held perception today that intensely-bred, modern varieties of flowers have lost their ability to produce and emit floral scent. Consumers often raise this complaint when purchasing flowering plants with which they have strong expectant associations with their floral scent characteristics (such as roses and carnations). This perception, correct or not, has been attributed to the idea that a large number of commercial flower varieties have lost their scent during the selection and breeding processes due to, on the one hand, a focus on maximizing post-harvest shelf-life, shipping characteristics, and visual aesthetic values (i.e., expansive color offerings, shape, free-flowering characteristics), and on the other hand, to the lack of selection for the scent trait. While not rigorously tested or examined, plant breeders have long viewed the biochemical processes of floral scent production as energy-intensive, and which if minimized or eliminated, would conserve the plant's energy resources for the production of more flowers and/or longer-lasting blooms. This is especially unfortunate as the sensory experience associated with floral scent is currently in strong demand by the consumer.

In an attempt to satisfy the consumer's demand for floral scent, there are several possibilities that can be considered. In one approach, older ornamental varieties that have been characterized as fragrant could be re-introduced into the marketplace. In many instances, however, the horticultural performance of these older varieties may disappoint the consumer as they may not compare well with today's modern varieties (e.g., they may have short-lived flowers). This may seriously limit their consumer appeal and likelihood of commercial success. In other cases, these older, so-called 'heirloom varieties' may no longer be in cultivation and the floral scent-associated genes residing in the germplasm of these plants may be unrecoverable.

In an attempt to impart fragrance to cut flower stems or even intact plants, a number of ideas have been advanced which rely upon exogenous applications of fragrant, volatile molecules. Occasionally, fragrances are added back to a cut flower arrangement by way of commercially-synthesized fragrances that are sprayed onto the flower arrangement. Many of such fragrances are supported in an alcohol-based carrier that evaporates upon application, allowing the fragrance to permeate back into the air over a limited time. Commonly, however, such fragrances are lost two to three days after application, although the appearance of the flowers may continue for seven to fourteen days, before wilting occurs.

A series of patents describe devices for imparting fragrance to flowering plants or cut flowers. U.S. Pat. No. 4,827,663 (Stern) describes a flower arrangement apparatus, and in particular, an improved stem support including an encapsulated stem-sustaining plant oil mixture whereby the cut flower's fragrance can be maintained commensurate with the life of the flower arrangement itself. In this invention, an improved cut stem support in conjunction with a water-dissolvable capsule composed of a cut flower-sustaining plant oil mixture is described. The additive oil mixture is thought to float on the water and over time be absorbed into the flowers. An improved fragrance is thus obtainable from the floating oils themselves, as well as the petal of the flowers, which are imagined to permeate still additional fragrance through ongoing cellular activities. However, Stern nowhere demonstrates that the various plant oil mixtures that are described are actually taken up by the plants (nor demonstrates that these fragrances are even capable of being affected by ongoing cellular activities) and later emitted from the plant cell surfaces.

In a related invention, U.S. Pat. No. 5,353,546 (Bock) teaches a combination vase and air fragrance dispenser comprising two vessels, one for holding natural or artificial flowers, the other for holding a fragrance-emitting material. The two-vessel construction ensures complete separation between the flower and air treatment material, preventing contamination of the flower. The flower holding vessel is capable of receiving water needed to keep natural flowers fresh.

Similarly, U.S. Pat. No. 5,477,640 (Holtkamp, Jr.) teaches a fragrance-emitting plant watering system, wherein a potted natural flowering plant is seated within a larger vase-like solid fragrance emitter. A wick transports water from a water reservoir to a potted plant. An air freshener cartridge for emitting a fragrance is provided in a separate compartment of the device.

Finally, U.S. Pat. No. 6,013,524 (Friars et al.) describes a 'living air freshener' comprising a dwarf flowering plant such as a miniature rose plant rooted in a transparent or non-transparent growth medium in a transparent vessel, with a natural or artificial fragrance composition added directly to the growth medium or to a second compartment in said vessel. This invention provides a living air freshener that offers both an attractive flower display and a natural or artificial air freshening fragrance. Unlike cut flowers, it is envisioned that this product will actually grow, flower and die providing both air freshening and an attractive flower display. Like U.S. Pat. Nos. 5,353,546 and 5,477,640, this invention teaches that the aromatic compounds can be natural or artificial which are chemically inert (i.e., non-utilizable) to the plant, such that the compounds can be added directly to the growth medium or to a separate chamber or compartment of the display vessel in case that the aromatic compound is adversely affected by periodic watering of the plant, or the chemistry of the aromatic compound is adverse to the plant roots.

Collectively, these patents teach methods to construct an apparatus for enhancing the fragrance of either cut flowers or potted plants in which fragrance compounds are supplied exogenously to the plant tissues. In a somewhat-related example, U.S. Pat. No. 5,635,443 (Lesenko) describes a composition for enhancing the fragrance of cut flowers by providing (a) at least one surfactant, (b) at least one fragrance, (c) at least one fragrance solvent, (d) water and other lesser components like sodium chloride, sodium bicarbonate and an antifoaming agent in a liquid composition. The inventor speculates that the fragrance compound would then be taken up through the cut end of the stem of a cut flower, transported to the petal tissue and emitted from the flower. However, U.S. Pat. No. 5,635,443, like U.S. Pat. No. 4,827,663, does not teach whether the fragrance supplied to the cut flower is actually emitted from the flower or foliage. Moreover, if fragrance is detected, the inventor does not address the possibility that the fragrance may be due to direct volatilization of the compound from the vase water, and not emitted from plant tissues (as is contemplated in U.S. Pat. No. 4,827,663 and others noted above).

Taken together, U.S. Pat. Nos. 4,827,663, 5,353,546, 5,477,640, 6,013,524, and 5,635,443 describe devices and compositions for imparting natural or artificial fragrances to cut flowers and flowering plants. However, these methods do not teach how to create, maintain, enhance or modify floral scent using the natural cellular activities of the plants to synthesize and emit floral scent. That is, these patents describe the addition of already-scented, often-synthetic, volatile fragrance molecules to liquid or semi-solid compositions for fragrance emission. In essence, these methods describe artificial fragrance dispensers that emit the fragrance of plant oils extracted from the flowers, foliage or other plant parts. In contrast, the invention described herein describes a composition and methods on how to create, maintain, enhance or modify floral scent by treatment of a cut flower or flowering plant not with a naturally-occurring or synthetic fragrance compounds but with a floral scent precursor molecule which is able to be converted to a floral scent molecule by the metabolic activities of the plant cells (bioconversion), or which is able to stimulate the emission of natural floral scent components from the plant. That is, the floral scent emission pattern of the plant is specifically modified through the metabolic engineering of floral scent biosynthetic pathway(s) by exogenous applications of floral scent precursor compounds.

As noted above, in recent years, biochemists and molecular biologists have begun to address the biochemical questions surrounding floral scent biosynthesis and emission, largely in model organisms like *Clarkia breweri* and, to a much lesser extent, *Antirrhinum majus* L. (or snapdragon). Flowers of *Clarkia breweri* ([Gray] Greene; Onagraceae) an annual plant native to California, emit a strong sweet fragrance consisting of 8 to 12 different volatiles. These volatiles are derived from two biochemical pathways, one leading to monoterpenoids, and the other to phenylpropanoids. In the former group, one is linalool. In the latter group three are the volatiles (iso)methyleugenol, benzylacetate, and methylsalicylate. In addition, the formation of methylbenzoate, another phenylpropanoid, in snapdragon flowers has been very recently reported (Bushue et al., 1999, in *Plant Biology '99, American Society of Plant Physiologists*, p. 80).

Terpenes, especially monoterpenes such as linalool, limonene, myrcene, and trans-ocimene, but also some sesquiterpenes such as farnesene, nerolidol, and caryophyllene, are common constituents of floral scent. They are also often found in vegetative tissues, where they serve mostly as defense compounds. In work done mostly with vegetative tissue, but also with daffodil petals, it was found that monoterpenes are synthesized in the plastidic compartment. In this cellular compartment, isopentenyl pyrophosphate (IPP) is derived from the mevalonate-independent "Rohmer" pathway (Lichtenthaler et al., 1997, *Plant Physiology* 101:643–652.). IPP can be isomerized to dimethylallyl diphosphate (DMAPP), and one molecule of IPP is condensed with one molecule of DMAPP in a reaction catalyzed by the enzyme geranyl pyrophosphate synthase (GPPS) to form geranyl pyrophosphate (GPP), the universal precursor of all the monoterpenes. Similar work with vegetative tissue has revealed that in the cytosol, IPP is derived from the mevalonic acid pathway (McCaskili and Croteau, 1998, *Trends in Biotechnology* 16:349–355), and two molecules of IPP and one molecule of DMAPP are condensed in a reaction catalyzed by the enzyme farnesyl pyrophosphate synthase (FPPS) to form farnesyl pyrophosphate (FPP), the universal precursor of all the sesquiterpenes (McGarvey and Croteau, 1995, *Plant Cell* 7:1015–1026).

The phenylpropanoids, which are derived from the amino acid, phenylalanine, constitute a large class of secondary metabolites in plants. Many are intermediates in the synthesis of structural cell components (e.g., lignin), pigments (e.g., anthocyanins), and defense compounds. These are not usually volatile. However, several phenylpropanoids whose carboxyl group at C9 is reduced (to either the aldehyde, alcohol, or alkane/alkene) and/or which contain alkyl additions to the hydroxyl groups of the benzyl ring or to the carboxyl group (i.e., ethers and esters) are volatiles.

Work with *C. breweri* flowers has now resulted in the identification and characterization of four enzymes that catalyze the formation of four individual floral volatiles: linalool, (iso)methyleugenol, benzylacetate, and methylsalicylate. The enzymes are, respectively, linalool synthase (LIS), S-adenosyl-L-Met:(iso) eugenol O-methyltransferase (IEMT), acetyl-CoA:benzylalcohol acetyltransferase (BEAT), and S-adenosyl-L-Met:salicylic acid carboxyl methyltransferase (SAMT) (Dudareva et al., 1996, *Plant Cell* 8:1137–1148; Wang et al., 1997, *Plant Physiology* 114:213–221; Dudareva et al., 1998, *Plant Journal* 14:297–304; Dudareva et al., 1998, *Plant Physiology* 116: 599–604; Wang and Pichersky, 1998, *Archives of Biochemistry and Biophysics* 349:153–160; Ross et al., 1999, *Archives of Biochemistry and Biophysics* 367:9–16). While IEMT and SAMT have relatively strict preferences for the substrates that they utilize [(iso)eugenol and salicylic acid, respectively], BEAT has been shown to utilize benzyl alcohol preferentially, but will also utilize other substrates like cinnamylalcohol and 2-napthaleneethanol very efficiently, to synthesize an array of aromatic compounds. LIS, like other monoterpene synthases, strictly utilizes GPP. Taken together, these results have established a substrate-product relationship for the bioconversion of non-fragrant floral scent precursors to fragrant floral scent components by the plant's enzymatic activities.

In *C. breweri* flowers, emission of the bulk of the volatiles occurs from the petals. Identification of the enzymes responsible for the formation of these volatile compounds has permitted investigators to determine how the levels of enzymatic activities are distributed in different floral parts and how they vary during flower development. When activity levels are calculated per total weight of each organ, the highest levels of activity of all these enzymes are found in the petals (Dudareva et al., 1998, *Plant Physiology* 116: 559–604). Other parts of the *C. breweri* flower, however, also contain detectable levels of activity, and the stigma actually contains higher levels of LIS specific activity (but because the mass of the stigma of *C. breweri* is so small compared with the mass of the petals, LIS in the petal still comprises the majority of activity present in the flower). The specific types of cells expressing the genes encoding LIS and IEMT were determined by in situ hybridization. The results indicate that in *C. breweri* flowers, these scent genes are expressed uniformly and almost exclusively in cells of the epidermal layer of petals and other floral parts (Dudareva et al., 1996, *Plant Cell* 8:1137–1148; Dudareva and Pichersky, 2000, *Plant Physiology* 122:627–633). Volatile compounds produced in epidermal cells can apparently escape directly into the atmosphere after being synthesized.

Throughout the lifespan of the flower, the activities of LIS, IEMT, SAMT and BEAT in *C. breweri* follow complex patterns. *C. breweri* flowers do not show marked differences in emission between day and night. *C. breweri* flowers follow a long-term pattern in which emission peaks within a few days of anthesis and then declines gradually. In *C. breweri*, the activities of scent enzymes follow two different patterns. The activities of the first group of enzymes, represented by LIS and SAMT, increase in maturing buds and young flowers, peaking about 12 to 24 hours ahead of peak volatile emission. LIS and SAMT activities then decline in old (5-day) *C. breweri* flowers, but remain relatively high (40%–50% from the maximum level) even though emission of linalool and methylsalicylate has practically ceased. The activities of the second group of enzymes, represented by IEMT and BEAT, show little or no decline at the end of the lifespan of the flower, although, again, emission of methyleugenol, isomethyleugenol, and benzylacetate virtually cease. A minor difference in developmental profiles of the latter two enzymes is that IEMT levels peak on Day 1 of anthesis and stay stable afterward (Wang et al., 1997, *Plant Physiology* 114:213–221), whereas BEAT activity does not peak until the 4th day after anthesis (Dudareva et al., 1998, *Plant Journal* 14:297–304). Overall, these studies showed that scent production in *C. breweri* is a complex process that involves spatial and temporal patterns of regulation that are not necessarily identical for all of the enzymes involved.

In related genetic studies, researchers have begun to clone the genes which encode these floral scent biosynthetic enzymes and are beginning to uncover the underlying molecular mechanisms that control floral scent production and emission, and, in some instances, how particular varieties or species lose their ability to emit fragrance. Expression of genes encoding floral scent biosynthetic enzymes in the *C. breweri* flower is temporally and spatially regulated during flower development. Dudareva et al. (1998, *Plant Journal* 14:297–304) demonstrated that BEAT expression is tissue-specific; it is not expressed at detectable levels in leaves, and that among floral organs, the bulk of the BEAT MRNA transcripts are found in the petals. Similarly, Dudareva et al. (1996, *Plant Cell* 8:1137–1148) reported that LIS expression is most abundant in the petals, stigma, style, and is not found in the vegetative parts of the plant. The mRNA's encoding LIS, IEMT, and BEAT are first detected in petal cells just before the flower opens, and their levels increase until they peak at or around anthesis and then begin to decline (Dudareva et al., 1996, *Plant Cell* 8:1137–1148; Dudareva et al., 1998, *Plant Journal* 14:297–304; Wang et al., 1997, *Plant Physiology* 114:213–221). For all of these three genes, peak levels of the mRNA's occur 1 to 2 days ahead of the peaks of enzyme activity and emission of the corresponding compound. These gene expression results taken together suggest the presence of a common regulatory mechanism for floral scent biosynthetic genes whose mRNA levels peak at or around anthesis.

Overall, the data show that a good positive correlation exists between the amount of mRNA, the amount of protein and enzymatic activity for each of these enzymes, and emission of the corresponding component up to the second or third day post-anthesis. But beyond that point, the levels of scent enzymes remain relatively high despite declining levels of the corresponding mRNA and also without the concomitant emission of volatiles (Dudareva et al., 1996, *Plant Cell* 8:1137–1148; Dudareva et al., 1998, *Plant Jour-* nal 14:297–304). These results also indicate that in *C. breweri* flowers, scent compounds are synthesized de novo in the epidermal cells of organs from which they are emitted (primarily the petals). Thus, those investigators concluded that the levels of activity of enzymes involved in scent production are regulated mainly at the mRNA levels at the site of emission.

The causes and consequences of appreciable levels of activity of biosynthetic enzymes in old flowers, without concomitant emission of the volatile products, were unknown. Nonetheless, the hereinbefore discussed investigators advanced several hypotheses to explain this result. First, they thought that it was possible that the biosynthetic pathways in which these enzymes participate are blocked elsewhere. Second, they thought that another possibility was that the products of the reactions catalyzed by these enzymes are required for processes other than scent emission in the flowers. Indeed, it has been found that the flowers of many species accumulate glycosides of scent compounds as they age. Such non-volatile glycosides are also sometimes found in buds, and were therefore originally hypothesized to be obligatory "scent precursors."However, closer examination has shown that, in most cases, an increase in emission of a particular volatile is not accompanied by a corresponding decrease in levels of the glycoside of this volatile, as would be expected by this hypothesis. The increased synthesis of such glycosides as the flowers age may account for the cessation of scent emission, although the specific roles of such glycosides in the flower remain to be determined. Finally, they thought that a third possibility was that as the flower ages, substrates may be diverted to other compartments and are not accessible to the scent biosynthetic enzymes. Whatever the explanation, it was abundantly clear that high levels of activity of biosynthetic enzymes without concomitant emission of the volatile products could be found in disparate metabolic pathways (e.g., BEAT in the phenylpropanoid pathway and LIS in the monoterpenoid pathway) within the same flower. According to these investigators, these observations suggested the presence of a common, globally-aoting regulatory mechanism for control of floral scent emission.

Biochemical and molecular analysis of scent production in other flowers from the *Clarkia* genus have yielded some early insights into the underlying basis for scent production. The genus *Clarkia,* which is subdivided into eight sections, is a member of the evening primrose family and contains 44 species. With the exception of the moth-pollinated *C. breweri,* all other species of the genus have essentially nonscented flowers that are pollinated mostly by bees. The flowers of *C. breweri,* a species believed to have evolved recently from the nonscented *C. concinna* (the only other member of section *Euchardium*), emits a relatively simple mixture of monoterpenoid and phenylpropanoid compounds, but primarily the monoterpenoid, linalool. Dudareva et al. (1996, *Plant Cell* 8:1137–1148) were able to demonstrate that a large increase in, and a wider distribution of, LIS activity in *C. breweri* flowers as compared to *C. concinna* flowers. These observations did not reveal whether such changes were brought about by changes in the level of LIS gene transcription or by changes at subsequent steps controlling gene expression. In later studies, these questions were answered as RNA gel blot analysis revealed that low levels of LIS transcripts were detected only in the stigma of *C. concinna* flowers, and no transcripts were detected in the petals, styles, stamens, or sepals. Moreover, no LIS protein could be detected in any *C. concinna* floral organ. Taken together, these results demonstrated that the level of LIS protein is tightly correlated with the steady state levels of LIS mRNA in *C. concinna,* and the very low levels of both help explain the low levels of linalool emitted from *C. concinna*. Thus, these investigators concluded that the major regulatory mechanism(s) for biosynthesis and emission of floral scent in *Clarkia* flowers (both *breweri* and *concinna*) were found at the transcriptional and translational levels of the floral scent biosynthetic enzymes themselves.

In connection with their research on this invention, the present inventors hypothesized that another possible, though yet undiscovered, explanation for a reduction in or lack of floral scent might be due to inadequate levels or inaccessible pools of floral scent precursors. Although the identity of floral scent precursors is known in some instances (e.g., GPP, FPP, (iso)eugenol, benzyl alcohol, salicylic acid), there is a large body of unknown facts concerning these precursors. In most cases, the complete biochemical pathway(s) leading to the floral scent precursors are unknown. Also, the size of the pools of the precursors is unknown as well and is often difficult to quantify, due in part to the difficult and complicated assays that are required for analysis. Finally, even if floral scent precursors are detected, that still does not address the question as to the site of biosynthesis within the plant. For example, the detection of benzyl alcohol in *C. breweri* flower petals does not fully guarantee that this floral scent precursor was synthesized in situ, but rather could have been transported to the petals from the sepals, or the foliage, or even the roots. Thus, there exists a myriad of questions about the location(s) of intracellular sites for biosynthesis, identity of metabolic pathways involved, plant tissue sources, and regulatory steps for floral scent precursor biosynthesis in plants.

The present invention arose as the result of research conducted by the inventors to determine whether the emission of floral scents from plants could be modified by manipulating the supply of floral scent precursor compounds to plants. As a result of this research, the inventors have discovered that by supplying floral scent precursors to cut flowers, they have been able to dramatically modify the floral scent emission pattern from cut flowers. Moreover, the inventors have discovered that the modified emission pattern is dependent upon the presence of the floral scent precursor. These discoveries have also been extended to include a potted flowering plant in which the floral scent precursor compound has been exogenously supplied as a spray application. Moreover, the inventors have further discovered that the emission of volatile floral scent compounds which are seemingly unrelated to the floral scent precursor supplied are also altered and modified by a yet-unknown cellular mechanism. Finally, the inventors have demonstrated that the presence of a floral scent precursor can negate the adverse effects that certain climatic conditions (e.g., refrigerated temperatures and an extended period of darkness) can impose upon floral scent emission from cut flowers. Taken together, the inventors have discovered that the multicomponent floral scent emission pattern of a flower can be maintained, enhanced or modified by supplying a single floral scent precursor to the plant.

SUMMARY OF THE INVENTION

In one embodiment, the present invention relates to a method for modifying the biosynthesis of at least one floral scent in a plant. The plant used in this method can be a potted plant, a hydroponically grown plant, a field grown plant, an in vitro grown plant, a greenhouse grown plant, or a plant grown in a bioreactor. Specifically, this method involves applying to a plant an effective amount of a composition containing at least one floral scent precursor which modifies the biosynthesis of a floral scent in a plant. The composition used in this method contains from about 1 ppm to about 1000 ppm of a floral scent precursor. Examples of floral scent precursors which can be used in this method include benzoic acid, phenylalanine, trans-cinnamic acid, benzylalcohol, salicylic acid, geranyl pyrophosphate, farnesyl pyrophosphate, jasmonic acid, eugenol or isoeugenol. In addition to the floral scent precursor, the composition can also contain nutrient sources, preservatives, excipients or additives.

In a second embodiment, the present invention relates to a method for modifying the emission of at least one floral scent from a plant. The plant used in this method can be a potted plant, a hydroponically grown plant, a field grown plant, an in vitro grown plant, a greenhouse grown plant, or a plant grown in a bioreactor. Specifically, this method involves applying to a plant an effective amount of a composition containing at least one floral scent precursor which modifies the emission of a floral scent from a plant. Preferably, as a result of performing this method, the emission of at least one floral scent from the plant is increased. The composition used in this method contains from about 1 ppm to about 1000 ppm of a floral scent precursor. Examples of floral scent precursors which can be used in this method include benzoic acid, phenylalanine, trans-cinnamic acid, benzylalcohol, salicylic acid, geranyl pyrophosphate, farnesyl pyrophosphate, jasmonic acid, eugenol or isoeugenol. In addition to the floral scent precursor, the composition can also contain nutrient sources, preservatives, excipients or additives.

In a third embodiment, the present invention relates to a method for modifying the biosynthesis of at least one floral scent in a plant cutting. Specifically, the method involves applying to a plant cutting an effective amount of a composition containing at least one floral scent precursor which modifies the biosynthesis of a floral scent in a plant, and a nutrient source. The composition used in this method contains from about 1 ppm to about 1000 ppm of a floral scent precursor. Examples of floral scent precursors which can be used in this method include benzoic acid, phenylalanine, trans-cinnamic acid, benzylalcohol, salicylic acid, geranyl pyrophosphate, farnesyl pyrophosphate, jasmonic acid, eugenol or isoeugenol. The composition used in this method contains from about 0.5% to about 10% by weight of a nutrient source. Preferably, the nutrient source is a carbohydrate, such as sucrose, fructose, glucose, galactose or raffinose. In addition to the floral scent precursor and nutrient source, the composition can also contain nutrient sources, preservatives, excipients or additives.

The hereinbefore described method can be used to modify the biosynthesis of at least one floral scent in a plant cutting which is subjected to refrigerated temperature and/or reduced light conditions. Refrigerated temperature conditions are those conditions wherein the temperature is in the range of from about 0° C. to about 20° C., preferably from about 2° C. to about 15° C. Reduced light conditions are those conditions where the cuttings are subjected to an absence or near-absence of light for a certain period of time. For example, the plant cutting can be subjected to such reduced light conditions for a period of from about 1 hour to about 240 hours, preferably from about 12 hours to about 168 hours.

In a fourth embodiment, the present invention relates to a method for modifying the emission of at least one floral scent from a plant cutting. Specifically, this method involves applying to a plant cutting an effective amount of a composition containing at least one floral scent precursor which modifies the emission of a floral scent from a plant, and a nutrient source. Preferably, as a result of performing this method, the emission of at least one floral scent from the plant cutting is increased. The composition used in this method contains from about 1 ppm to about 1000 ppm of a floral scent precursor. Examples of floral scent precursors which can be used in this method include benzoic acid, phenylalanine, trans-cinnamic acid, benzylalcohol, salicylic acid, geranyl pyrophosphate, farnesyl pyrophosphate, jasmonic acid, eugenol or isoeugenol. The composition used in this method contains from about 0.5% to about 10% by weight of a nutrient source. Preferably, the nutrient source is a carbohydrate, such as sucrose, fructose, glucose, galactose or raffinose. In addition to the floral scent precursor and nutrient source, the composition can also contain nutrient sources, preservatives, excipients or additives.

The hereinbefore described method can be used to modify the emission of at least one floral scent from a plant cutting which is subjected to refrigerated temperature and/or reduced light conditions. Refrigerated temperature conditions are those conditions wherein the temperature is in the range of from about 0° C. to about 20° C., preferably from about 2° C. to about 15° C. Reduced light conditions are those conditions where the cuttings are exposed to an absence or near-absence of light for a certain period or length of time. For example, the plant cutting can be subjected to such reduced light conditions for a period of from about 1 hour to about 240 hours, preferably from about 12 hours to about 168 hours.

In a fifth embodiment, the present invention relates to a method of attracting a pollinator, such as a honeybee or moth, to a plant. Specifically, this method involves applying to a plant an effective amount of a composition containing at least one floral scent precursor which increases the emission of a floral scent from a plant, wherein said increased emission of said floral scent from the plant is sufficient to attract at least one pollinator to said plant. The composition used in this method contains from about 1 ppm to about 1000 ppm of a floral scent precursor. Examples of floral scent precursors which can be used in this method include benzoic acid, phenylalanine, trans-cinnamic acid, benzylalcohol, salicylic acid, geranyl pyrophosphate, farnesyl pyrophosphate, jasmonic acid, eugenol or isoeugenol. In addition to the floral scent precursor, the composition can also contain nutrient sources, preservatives, excipients or additives.

In a sixth embodiment, the present invention relates to a method for attracting a plant pest, such as an insect, to a plant. Specifically, this method involves applying to a plant an effective amount of a composition containing at least one floral scent precursor which increases the emission of a floral scent from a plant, wherein said increased emission of said floral scent is sufficient to attract at least one plant pest to said plant. The composition used in this method contains from about 1 ppm to about 1000 ppm of a floral scent precursor. Examples of floral scent precursors which can be used in this method include benzoic acid, phenylalanine, trans-cinnamic acid, benzylalcohol, salicylic acid, geranyl pyrophosphate, farnesyl pyrophosphate, jasmonic acid, eugenol or isoeugenol. In addition to the floral scent precursor, the composition can also contain nutrient sources, preservatives, excipients or additives.

In a seventh embodiment, the present invention relates to a method for increasing the floral scent of a plant in order to facilitate the identification of at least one volatile compound from said plant. Specifically, this method involves applying to a plant an effective amount of a composition containing at least one floral scent precursor which increases the emission of a floral scent from a plant, wherein said increased emission of said floral scent is sufficient to facilitate the identification of at least one volatile compound from said plant. The composition used in this method contains from about 1 ppm to about 1000 ppm of a floral scent precursor. Examples of floral scent precursors which can be used in this method include benzoic acid, phenylalanine, trans-cinnamic acid, benzylalcohol, salicylic acid, geranyl pyrophosphate, farnesyl pyrophosphate, jasmonic acid, eugenol or isoeugenol. In addition to the floral scent precursor, the composition can also contain nutrient sources, preservatives, excipients or additives.

DETAILED DESCRIPTION OF THE INVENTION

As discussed previously, many plants emit a floral scent, and such scents can attract a variety of animal pollinators, mostly insects. The floral scents emitted by plants are composed of a varying number, kind and amount of fragrant volatile compounds. Examples of some of the fragrant volatile compounds which make up a floral scent in plants include, but are not limited to, terpenes, particularly monoterpenes such as linalool, limonene, myrcene, and trans-ocimene and sesquiterpenes such as farnesene, nerolidol, and caryophyllene and phenylpropanoids, such as, methylbenzoate, isomethyleugenol, benzylacetate and methylsalicylate.

The present invention relates to methods for modifying the biosynthesis (production) and/or emission of at least one floral scent from a plant and/or plant cutting. More specifically, the methods of the present invention employ certain compositions which can be used to modify the quantity or amount of one or more fragrant volatile compounds emitted from a plant and/or plant cutting. Additionally, these compositions can be used to alter or change the quality of at least one floral scent emitted from a plant and/or plant cutting. Moreover, the present invention further relates to methods for modifying the biosynthesis (production) and/or emission of a floral scent from a plant cutting which has been subjected to refrigerated and/or reduced light conditions.

As used herein, the term "plant" refers to a whole live plant as well as to any part, tissue or organ from a live plant. For example, the term "plant" includes fruit,-flowers, tubers, roots, stems, hypocotyls, leaves, petioles, petals, seeds, tissue culture material (for use in bioreactors), etc. The term "plant" also includes plants which have been transformed using genetic engineering techniques and which contain at least one exogenous gene of interest. For example the exogenous gene may encode an enzyme which converts a floral scent precursor into a floral scent molecule.

As used herein, the term "fragrant volatile" or "fragrant volatile compound" means a chemical compound that imparts a pleasing or pleasant odor and evaporates readily, particularly at low temperatures (i.e. from about 0° C. to about 30° C.). Examples of a "fragrant volatile" or "fragrant volatile compound" include, but are not limited to: (1) terpenes, particularly monoterpenes such as linalool, limonene, myrcene, and trans-ocimene and sesquiterpenes such as farnesene, nerolidol, and caryophyllene; as well as (2) phenylpropanoids, such as, methylbenzoate, isomethyleugenol, benzylacetate and methylsalicylate.

As used herein, the term "emission pattern" refers to the chemical composition of a floral scent, which typically has a single or multiple component(s) and which is volatilized over time and during specific developmental phases in a plant.

As used herein, the term "floral scent precursor" means a natural or synthetic biologically-relevant compound, which preferably, but may not, be characterized as having non-fragrance-emitting properties, and which can be enzymatically converted to a modified biologically-relevant compound having fragrance-emitting properties. The term "floral scent precursor" also includes natural or synthetic functional analogs of these biologically-relevant compounds which may or may not be enzymatically converted, but may be functioning additionally or alternatively as a general inducer or activator of floral scent biosynthesis and/or emission.

The term "effective amount of a composition" as used herein means such amount as is necessary for performing the function of the composition for which an effective amount is expressed. The exact amount required for use in the methods of the present invention will vary from method to method depending on the plant species being treated, the environmental conditions under which such plants will be treated, the identity of the floral scent precursor, the method of application, the duration of the exposure, etc. Thereupon, it is not possible to specify an exact "effective amount". However, an appropriate effective amount can be determined by one of ordinary skill in the art using routine experimentation.

The term "floral scent" as used herein means a composition of one or more biologically-synthesized fragrant volatile compounds that imparts fragrance-emitting properties, and which is produced by plant tissues, most commonly arising from, but not limited to, the flower.

The term "reduced light conditions" are those conditions where the cuttings are subjected to an absence or near-absence of light for a certain period of time.

In one embodiment, the present invention relates to methods for modifying the biosynthesis (production) and/or emission of at least one floral scent from a plant. The methods involve applying to a plant an effective amount of a composition which contains at least one floral scent precursor(s) which is capable of modifying the biosynthesis (production) and/or emission of a floral scent from a plant. More specifically, the floral scent precursor(s) contained in the composition is capable of increasing or decreasing the quantity or amount of at least one floral scent biosynthesized (produced) and/or emitted from a plant. Additionally, the floral scent precursor(s) contained in the composition can also be capable altering or changing the quality of a floral scent and/or fragrance biosynthesized (produced) and/or emitted from a plant. As demonstrated herein in Example 7, the ratio of monoterpenoid:phenylpropanoid compounds in the snapdragon floral scent (ocimene/myrcene:methylbenzoate) was modified after a spray application of benzoic acid, thus changing or altering the composition, and hence the quality of the floral scent which was biosynthesized and eventually emitted from the plant.

Examples of floral scent precursors that can be used in the composition include, but are not limited to, benzoic acid, phenylalanine, trans-cinnamic acid, benzylalcohol, salicylic acid, GPP, FPP, jasmonic acid, eugenol or isoeugenol.

The composition used in the hereinbefore described methods can contain from about 1 ppm to about 1000 ppm (wherein 1 ppm equals 1 μg/ml) of a floral scent precursor which enhances the biosynthesis (production) and/or emission of a floral scent from a plant, preferably from about 25 ppm to about 500 ppm of a floral scent precursor which enhances the biosynthesis (production) and/or emission of a floral scent from a plant, and most preferably from about 50 ppm to about 200 ppm of a floral scent precursor which enhances the biosynthesis (production) and/or emission of a floral scent from a plant. Additionally, the composition preferably has a pH of from about 3.0 to about 8.0.

Additionally, it is also preferred that the composition contain an acceptable carrier for the floral scent precursor such as water. However, other carriers, such as organic solvents, can also be contemplated. Alternatively, the composition can be provided in dried form and reconstituted in water or other acceptable carrier.

Optionally, the composition can also contain preservatives (such as bacteriocides), nutrient sources, excipients or additives, such as, but not limited to, antifoaming agents and surfactants. A used herein, the term "nutrient source" refers to a compound or combination of compounds which are metabolized by the plant for the purpose of supplying energy to the plant. An example of a nutrient source is a carbohydrate such as sucrose, fructose, glucose, galactose or raffinose.

The composition can be applied to a potted plant, a hydroponically-grown plant, a plant grown in a field, an in vitro grown plant, a greenhouse-grown plant, or to a plant grown in a bioreactor.

The composition can be applied to the plant in any form and manner. For example, the composition can be applied as spray or simply in liquid form. Alternatively, the plant may be soaked or drenched with the composition of the present invention.

In another embodiment, the present invention relates to methods for modifying the biosynthesis (production) and/or emission of a floral scent from a plant cutting. The methods involve exposing a plant cutting to an effective amount of a composition which contains at least one floral scent precursor which is capable of modifying the biosynthesis (production) and/or emission of a floral scent from a plant cutting. The composition must also contain at least one nutrient source. More specifically, the floral scent precursor(s) contained in the composition is capable of increasing or decreasing the quantity or amount of at least one floral scent biosynthesized (produced) and/or emitted from a plant cutting. Additionally, the floral scent precursor(s) contained in the composition may also be capable altering or changing the quality of a floral scent and/or fragrance produced and/or emitted from a plant. Moreover, the present invention further relates to methods for modifying the biosynthesis (production) and/or emission of a floral scent from a plant cutting which is subjected to refrigerated temperature and/or reduced light conditions. Like the methods described above, these methods involve exposing a plant cutting to an effective amount of a composition which contains at least one floral scent precursor which is capable of modifying the biosynthesis (production) and/or emission of a floral scent from a plant cutting which is subjected to refrigerated and/or reduced light conditions. The composition may also optionally contain at least one nutrient source.

As also discussed above, the composition used in the hereinbefore described methods contains at least one floral scent precursor which is capable of modifying the biosynthesis (production) and/or emission of a floral scent from the plant cutting or modifying the biosynthesis (production) and/or emission of a floral scent of a plant cutting which is subjected to refrigerated and/or reduced light conditions. The composition may also optionally contain a nutrient source. Examples of floral scent precursors that can be used in the present invention include, but are not limited to, benzoic acid, phenylalanine, trans-cinnamic acid, benzylalcohol, salicylic acid, GPP, FPP, jasmonic acid, eugenol or isoeugenol.

The composition employed in the hereinbefore described methods can contain from about 1 ppm to about 1000 ppm of a floral scent precursor which enhances the biosynthesis (production) and/or emission of floral scent from a plant cutting, preferably from about 25 ppm to about 500 ppm of a floral scent precursor which enhances the biosynthesis (production) and/or emission of floral scent from a plant cutting, and most preferably from about 50 ppm to about 200 ppm of a floral scent precursor which enhances the biosynthesis (production) and/or emission of floral scent from a plant cutting.

The composition may optionally contain a nutrient source. The composition for use with the methods described herein does not need to simultaneously contain both a floral scent precursor and a nutrient source when applied to a plant cutting. More specifically, a plant cutting could first be treated with a floral scent precursor and then at a later period in time be subsequently treated with a nutrient source, or vice versa. For example, freshly-harvested flowers could be transiently treated (or "pulsed") with a floral scent precursor, such as benzoic acid alone to "load up" the plant cutting with said floral scent precursor. The "pre-loaded" cutting would then contain sufficient amounts of floral scent precursor for the lifetime of the cutting, and then would only require the presence of a nutrient source for modification of the floral scent emitted. It is contemplated herein that with some plant cuttings, even the addition of a nutrient source might be optional since the cutting could have stored away adequate levels of nutrients.

The nutrient source contained in the composition is a compound or combination of compounds which iscapable of being metabolized by the plant for the purpose of supplying energy to the plant cutting. Preferably, the nutrient source is a carbohydrate. Examples of suitable carbohydrates that can be used in the composition include sucrose, fructose, glucose, galactose or raffinose. The nutrient source is present in the composition in the amount of from about 0.5% to about 10% by weight of the composition, most preferably from about 1.0% to about 7% by weight of the composition.

As mentioned previously, the hereinbefore described composition can be used in methods to modify the biosynthesis (production) and/or emission of a floral scent from a plant cutting which is subjected or exposed to refrigerated and/or reduced light conditions. In commercial cut flower production areas, a ubiquitous and absolutely essential growing practice is to harvest the flowers and transport them immediately to a refrigerated area to remove the 'field heat' from the flower bunches. Over the years, it has become firmly established that maintaining cut flowers under refrigerated conditions is necessary to maintain the freshness of the flower-bearing cut stem. In fact, cut flowers remain at refrigerated temperatures throughout the packaging, shipping, and distribution phases of the product. It is not until the consumer purchases the cut flowers at the retail outlet that the flowers are finally restored to ambient temperature on a full-time basis. This practice is designed exclusively to maximize the vase life of the cut flower for the end user, the consumer.

At the same time, current commercial cut flower production areas are often located overseas now due to optimum year-round growing conditions and a plentiful source of inexpensive labor. This demands that flowers be packaged and shipped for long-distance travel, which often means that the flowers are maintained under conditions of constant darkness for extended periods of time.

Thereupon, as discussed previously, the hereinbefore described composition can also be used in methods to modify the biosynthesis (production) and emission of a floral scent from a plant cutting which has been subjected to refrigerated and/or reduced light conditions. The methods involve exposing a plant cutting which has been subjected to refrigerated and/or reduced light conditions to the hereinbefore described composition containing at least one nutrient source and at least one floral scent precursor which is capable of modifying the biosynthesis (production) and/or emission of a floral scent from the plant cutting which has been exposed to refrigerated and/or reduced light conditions. The term "refrigerated conditions" as used herein refers to those natural or artificially created temperatures in the range of from about 0° C. to about 20° C., preferably from about 2° C. to about 15° C. The plant cutting may be exposed to such reduced light conditions for a period of from about 1 hour to about 240 hours, preferably for a period of from about 12 hours to about 168 hours. The composition described herein can be applied to a plant cutting either before or after exposure to said refrigerated temperature and/or reduced light conditions.

Preferably, the composition contains an acceptable carrier for the floral scent precursor such as water. However, other carriers, such as organic solvents, can also be contemplated. Alternatively, the composition can be provided in dried form and reconstituted in water or other acceptable carrier. Moreover, it is preferred that the composition have a pH of from about 3.0 to about 8.0.

The plant cutting can be exposed to the composition by simply adding the composition to a container (such as a vase, a bucket or pail, or other holding apparatus) which contains the plant cutting.

Optionally, the composition can also contain preservatives (such as bacteriocides), excipients or additives, such as, but not limited to, antifoaming agents and surfactants.

In another embodiment, the present invention relates to a method for attracting a pollinator, such as a honeybee or moth, to a plant. The method involves applying or exposing a plant to an effective amount of a composition which contains at least one floral scent precursor which is capable of modifying the emission of a floral scent from a plant. Preferably, the emission of a floral scent is increased in said plant. Thereupon, the increase in the emission of a floral scent or the emission of a unique floral scent from the plant as the result of the application composition can be used to attract a pollinator to said plant. The composition that can be used in this method is the same composition described previously for use in modifying the biosynthesis (production) and/or emission of a floral scent from a plant.

Flowers of many plants attract pollinators by producing and emitting low-molecular weight fragrant volatile compounds. The scent emitted by such flowers is often a complex mixture of low molecular weight compounds, and the relative abundances and interactions of the constituents give the flower its particular characteristic fragrance. Floral scents have been demonstrated to function as long and short-distance attractants and nectar guides to a variety of animal pollinators. Moreover, insects are able to distinguish between complex floral scent mixtures. Discriminatory visitation based on floral scent has important implications for population structure and reproductive isolation in both temperate and tropical plant species. Thus, floral scent is of paramount importance to plant reproduction and evolution.

Several thousand fragrant volatile compounds have been identified from various floral scents, mostly by steam distillation or headspace trapping in combination with gas chromatography-mass spectrometry (hereinafter "GC-MS"). Most of these compounds are either terpenoids, benzenoid compounds, or acyl lipid derivatives. For example, monoterpenoids are a large and diverse group of natural products. Due to their volatility, and thus their ability to be perceived at a distance, they are often involved in plant-insect interactions. Monoterpenes are derived from the ubiquitous isoprenoid intermediate, GPP, by a class of enzymes called monoterpene synthases (also termed cyclases when they catalyze the formation of cyclic products). Although many monoterpene synthases from plants have been described, only a few of these enzymes have been purified to homogeneity and characterized. In addition, few of the genes encoding these enzymes have been identified.

Thereupon, the hereinbefore described compositions can be used in a method to manipulate and modify the floral scents of a plant for the express purpose of impacting plant-insect interactions. The manipulation and modification of such floral scents are important as certain plants require pollinators that are attracted by floral scents. For example, some scented tropical trees introduced to the temperate zone are poorly pollinated, with a resulting poor yield, because their scent does not "appeal" to the local insects. The modification of floral scents as described herein allows for the manipulation of such traits and the enhancement of the attractiveness of such flowers to local pollinators. The present invention offers a way to amplify the biosynthesis and emission of fragrant volatile compounds from plants to enhance the attractiveness of such flowers to local pollinators, either through elevated concentrations of the floral scent (the more concentrated scent being more attractive to the pollinators), through longer-distance signaling (the increased fragrance emission attracts pollinators from further distances) or modified floral scents with increased insect-attractant properties.

For example, the white-lined sphinx moth, *Hyles lineata* L., is the most widely distributed hawkmoth species in the world. Raguso et al. (1996, *Journal of Chemical Ecology* 22:1735–1766) noted that hawkmoths are important pollinators of *Clarkia breweri* in the central Coast Range Mountains of California. They tested the olfactory sensitivity of *H. lineata* moths by measuring their electroantennogram (EAG) responses to the floral scent compounds of *C. breweri*. EAG's have been used to assess the olfactory sensitivities of agriculturally-important moth species in response to host plant volatiles. From this investigation, they determined that the EAG response was especially strong for methylbenzoate, indicating that this floral scent molecule evokes a strong olfactory response in this hawkmoth species. The present inventors contemplate that a plant treated with a floral scent precursor like benzoic acid to increase its floral scent (e.g., methylbenzoate) emission could influence the flight orientation and feeding behaviors of the local pollinators, thereby enhancing the overall levels of successful pollination events.

Similarly, but in a converse manner of thinking and as will be further described herein below, the present inventors further contemplate that a plant treated with a floral scent precursor like benzoic acid for the purpose of increasing its floral scent (e.g. methylbenzoate and/or monoterpenoids) emission might influence the flight orientation and feeding behaviors of the local plant pests (i.e. act as an attractant), thereby reducing the visitations, and by extension, herbivorous damage to the (adjacent) agricultural or horticultural crop of interest.

In yet another embodiment, the present invention relates to a method for modifying the floral scent of a plant and/or plant cutting in order to facilitate the identification of at least one fragrant volatile compound from the plant and/or plant cutting. The method involves applying to or exposing a plant and/or plant cutting an effective amount of at least one of the hereinbefore described compositions which contains at least one floral scent precursor which is capable of modifying the emission of a floral scent from a plant or plant cutting. If the composition is to be applied to a plant cutting, it may also optionally contain a nutrient source as described previously. Preferably, the hereinbefore described compositions cause an increase in the emission of a floral scent from a plant or plant cutting. This increase in the emission of a floral scent can be used to facilitate the identification of at least one fragrant volatile compound from the plant and/or plant cutting.

More specifically, although perfumers still survey natural sources for novel fragrance, this information is most often used in directing organic syntheses of compounds to imitate natural floral scents or fragrances or to create new combinations of floral scents or fragrances. In some cases, emission rates from a particular flower may be inadequate to accurately measure the overall composition of the floral scent. Therefore, the methods described herein can be used for increasing the floral scent emissions from a plant or plant cutting in order to facilitate the identification of specific fragrant volatile compounds (both identity and relative amounts) produced by the plant or plant cutting. As discussed previously, the method involves applying or exposing to a plant or plant cutting one of the hereinbefore described compositions which contains a compound which is capable of modifying (preferably, by increasing) the emission of a floral scent from a plant or plant cutting. For example, an inducer of fragrance emission, such as benzoic acid, can be used to increase the floral emissions from a plant. The resulting emission analysis can then be used to provide direction in the organic synthesis of a compound or combination of compounds to copy the natural fragrance or to create a new fragrance, thereby providing the consumer with additional new and perhaps exotic perfume purchase options.

In another embodiment, the present invention relates to methods for increasing the biosynthesis and/or emission of fragrant volatile compounds in plants or plant cuttings in order to enhance the flavors and fragrance in leaves, fruit or seed produced by such plants. The method involves applying or exposing a plant or plant cutting one of the hereinbefore described compositions. If the composition is to be applied to a plant cutting, it may also optionally also contain a nutrient source as described previously. It is known in the art that the perception of taste and flavors are very closely linked to the levels of fragrant volatile compounds produced by fruits and vegetables. In fact, this concept is described in U.S. Pat. No. 5,367,899 to Mookherjee et al. Mookherjee et al. describe a continuous process for qualitatively and quantitatively analyzing the aroma emitted and the rates of emission of the components thereof from a portion of the outer surface of a living fruit. This analysis is conducted in an enclosed 3-dimensional space proximate to the portion of the outer surface of said living fruit, while simultaneously using an aroma trapping device connected to the enclosed 3-dimensional space. The resulting analysis is used to prepare perfume compositions, perfumed articles and colognes.

Also described is an apparatus for carrying out such a process. Thereupon, the compositions described for use in the other methods described herein can be employed as a "natural flavoring" agent to enhance the flavors of grains, fruits such as strawberries, peaches, apples, oranges, lemons, limes, plums, cherries, raspberries, blackberries, tomatoes, etc., and vegetables such as peppers, melons, cucumbers, squash, watermelons, etc.

In another embodiment, the present invention relates to a method for attracting a plant pest to a plant. The method involves applying to a plant an effective amount of the hereinbefore described compositions which contains at least one floral scent precursor which is capable of modifying (preferably, by increasing) the emission of a floral scent from a plant. Such an increase in emission of a floral scent or the emission of a unique floral scent from the plant can be used to attract a pest to said plant. More specifically, the composition described previously for use in modifying the biosynthesis (production) and/or emission of a floral scent from a plant can also be used in this method as well.

Semiochemicals are plant-produced compounds which act by diffusion through air to produce behavioral responses in associated insect species. Kairomones are those semiochemicals which act to benefit the receiving species. Allomones are those which benefit the sending species. Synomones, e.g., floral volatiles involved in pollination, benefit both the emitting plant, through pollination, and the perceiving insect by rewards of nectar and pollen or through more intangible ecological rewards of aggregation or lek formations which lead to mating.

One report describing pest attraction to compounds appeared in Morgan et al. (1928, *J Econ. Entomol.* 21:913). This collection of preliminary results on the chemotropic response of certain insects included the observation that the spotted cucumber beetle was attracted to cinnamaldehyde and cinnamyl alcohol. The chrysomelid genera *Diabrotica* and *Acalymma* contain numerous pest species, including the western, northern, and southern corn rootworms, the spotted cucumber beetle, and the striped cucumber beetle.

The western, northern, and southern corn rootworms are the most expensive insect pests of North America and annually cost U.S. farmers approximately one billion dollars in yield loss and in cost of preventative treatments with soil insecticides. The era of relatively cheap crop protection against these pests has ended because of generalized rootworm resistance to organochlorine insecticides and the withdrawal of registrations for these insecticides by the U.S. EPA due to widespread environmental contamination. The newer organophosphorous and carbamate insecticides are more expensive and subject to accelerated microbial degradation in soils and a rapid loss of activity. Furthermore, due to the persistence of many of these soil insecticides, groundwater and surface run-off pollution is of much concern to state and federal agencies. Because of the uncertain performance and safety of the major products currently used for larval rootworm control, such as carbofuran (Furadan™), isofenphos (Amaze™), phorate (Thimet™), terbufos (Counter™), a technological void exists for controlling these pests. Even standard cultural methods of pest management such as crop rotations of corn-soybean-corn and corn are endangered as evidence exists that the northern corn rootworm can undergo an extended diapause for two seasons. Hence, the benefits of yearly crop rotation are threatened.

Present soil insecticide technology for corn rootworm control is rapidly becoming unworkable. The use of volatile attractants, singularly and in combinations with other control methods, can become the basis for a new integrated pest management (hereinafter "IPM") technology for rootworm control that is economically favorable for the farmer and certainly much less environmentally objectionable. In this regard, *Diabrotica* and *Acalymma* are known to show a close association with host plants of the family Cucurbitaceae, particularly with the genus *Cucurbita*. Adult beetles are most commonly found in the blossoms of *Cucurbita* species where they feed on pollen (in staminate flowers) and on nectar. In most instances, adult beetles showed a preference for the blossoms of *C. maxima* Duchesne cultivars over those of *C. pepo* L. and *C. moschata* Poir. The blossom characteristics, i.e., color, size, shape, and/or fragrance, responsible for this preference are not fully understood, although *Diabrotica* attraction to certain semiochemicals has been reported.

The hereinbefore described composition can be used as a lure for attracting and controlling certain pest species. Specifically, the compositions described for use in the previously described methods herein can further be used to increase the biosynthesis (production) and/or emission of one or more fragrant volatile compounds found in flower blossoms, or analogs thereof, in order to act as a lure to prevent certain pest species from attacking and destroying a crop of-interest. The fragrant volatile compounds emitted by a plant in response to treatment with such a composition can act as a lure, either alone or in combination with other lures, insecticides, and/or compulsive feeding stimulants. For example, a neighboring field can be populated with plants which are treated at some point during their growth phase with the composition in order to enhance or increase the biosynthesis and emission of fragrant volatile compounds. These fragrant volatile compounds are capable of attracting and luring pests away from an adjacent field in which the commercial crop of interest is being grown. Alternatively, rows in the same field can be interplanted with fragrant volatile-attracting plants and the desired crop of interest. At an appropriate time(s) during the growing season, the composition can be applied to the fragrant volatile-attracting plants in order to induce the biosynthesis (production) and/or emission of a fragrant volatile compound in order to minimize pest damage to the crop of interest.

Plant-derived fragrant volatile compounds have high commercial value as essential oils. Therefore, in another embodiment, the present invention relates to methods for producing new versions and types of essential oils. For example, treatment of an essential oil-producing plant with an appropriate precursor compound like GPP could increase the biosynthetic rate of monoterpenoid production (e.g., linalool and limonene), thereby increasing the proportion of monoterpenoids in the final essential oil product. Essential oils have commercial value for perfumery, flavoring and as industrial raw materials (see Table 1). The term "essential oil" is accredited to Paracelsus, a 16th century physician who believed the oil extracted from a vegetable substance contained the total odor or flavor and was the quintessence or fifth vital principal. Oils have been used throughout the ages, from Egyptians through to Greeks for anointment or for cooking and later for medicinal purposes. Gradually though, essential oils were used more and more for flavoring and perfumery so that by the end of the 19th century, there was a flourishing essential oils industry in countries such as France and North America. Today, over 3000 essential oils are known, of which several hundred are available commercially.

Essential oils are obtained as an odoriferous product when certain plant material is subject to physical processing such as distillation, expression or solvent extraction. Essential oils occur in many different parts of a plant including leaves, bark, berries, and exudate such as gums, resins, and balsams. The function of essential oils in plants is not fully understood. Essential oils often show bacteriostatic properties and some are bactericidal with evidence to show how essential oils can be used to preserve food and cosmetics against microbial spoilage. Essential oil-containing exudate, such as gums and resins, are produced by plants to prevent loss of moisture or attack by parasites when damaged. Most components of essential oils are secondary metabolites and are produced as intermediates or as side reactions during the production of the main plant components or during metabolism. Bacteriological and antioxidant properties shown by the oils of cloves, thyme, bay, origanum, sage and rosemary can be related to the high concentration of phenolic compounds such as rosmaridiphenol.

Essential oil crops are grown all around the world (see Table 1) and cultivation of hybrid high-yielding strains has kept pace with improvements in agricultural methods. The essential oil can occur in various parts of the plant, these being processed to yield the oil. Generally, this processing involves distillation and since it is not economical to transport bulky plant material, distillation often occurs in or close to the field where the plant is harvested. Mobile stills may be used which means processing often takes place under primitive conditions resulting in contamination of the oil with glycerides, tannins or minerals and sometimes involving complex formation with iron for example.

Steam distillation is most widespread and used for all oils except those with significant amounts of non-volatile or heat sensitive compounds. These are solvent extracted, perhaps using carbon dioxide in critical fluid extraction. Some oils are expressed e.g., citrus using modern high-speed equipment, and many flower oils are extracted with solvents. Typical yields are one percent or two percent but would cover the range 0.1 to 15 percent. The oils are generally liquid, although some are semi-solid or solid. Often the first extraction is further processed to concentrate, purify or extract particular components.

Rectification is the name given to a process of fractional distillation to improve the properties of an oil. Water can be removed, the terpene content adjusted and the color improved. Dimethyl sulfide is removed from peppermint oil in this way to improve its properties in flavoring applications, and the cineole content of eucalyptus oil is increased by removing unwanted terpenes and residues.

Most essential oils are approved for flavor uses, thus physiological properties must be considered. Work with experimental animals has been reported over the years, dermal and oral LD50 results being published in Monographs by the Research Institute for Fragrance. The effects on man have not been documented to any great extent, although where accidents have occurred materials can be seen to be toxic. Table 1 below lists some typical essential oils and their main uses.

TABLE 1

A Compilation of Common Essential Oils, Their Origins and Uses

| Oil | Country of Origin | Main Constituents | Main Use |
|---|---|---|---|
| Clove Leaf | Madagascar | Eugenol and its Acetate Caryophyllene | Toothpaste |
| Angelica (seed & root) | Europe | Alpha-Pinene, L-Carvone, Limonene, Beta-Phellandrene | Beverages |

TABLE 1-continued

A Compilation of Common Essential Oils, Their Origins and Uses

| Oil | Country of Origin | Main Constituents | Main Use |
|---|---|---|---|
| Anise Seed | China | Macrocyclic musks | Musks |
| Caraway | Netherlands, Poland | D-Carvone, Limonene | General Spice Flavors |
| Cinnamon | Sri Lanka, Vietnam | Cinnamic Aldehyde Eugenol | General |
| Dill (weed) | USA, Europe, India | D-Carvone, Limonene | Spice Flavors |
| Garlic | Europe, Egypt | Diallyl-Disulfide allyl, isothiocyanate | Savory Flavors |
| Ginger Oil | China, Africa, Far East | Zingibevenes, Citral, Curcumenes | Ginger flavors drinks |
| Grapefruit | USA, Israel | Limonene, Nootkatoone | Confection Soft drinks |
| Lemongrass | India, China, South America | Citral | Isolation of citral for soft drinks |
| Lemon | USA, Sicily | Limonene, Terpinene, Citral, Pinene | Soft drinks Confectionery Dairy |
| Lime | Mexico, West Indies | Citral, Limonene, Cineol | |
| Litsea Cubeba | China Far East | Citral | Isolation of citral for flavor and fragrance applications |
| Mandarin Oil | Italy, Spain, South America | n-Methyl, methyl, anthranilate | soft drinks and liquors |
| Mint (a) Mentha Arvensis | Brazil, China | L-menthol and its Acetate and Menthone | Toothpastes, Mouthwashes, Confectionery |
| Mint (b) Mentha Piperita | USA, Europe | L-menthol & its Acetate & Menthol & Menthofuran | As above but better quality |
| Spearmint | USA, China | L-Carvone, Limonene | Chewing gum, Toothpaste, Confectionery |
| Onion | Egypt Europe | Aliphatic Sulfides | Savory flavors |
| Sweet Orange | USA, Brazil, Australia, Mediterranean Countries | Limonene | Soft drinks, Confections |

Most essential oils are generally recognized as safe by the Food and Drug Authority in the USA and they are classified as natural products. Some oils can be used for both flavor and fragrance while others may produce irritation and therefore are not allowed for use in fragrance. In the future, it is unlikely that new oils or sources of oils will be identified that will be of commercial significance. However, "new" versions of currently available products are likely. Thereupon, the composition of the present invention can be used to produce novel versions of currently available essential oils. Moreover, the composition of the present invention can be used to increase the yields of essential oils from raw plant material. Increased yields of essential oils thereby provides more favorable process economics of extraction for the commercial extractors.

In yet another embodiment, the present invention relates to methods for modifying the levels of pest and pathogen resistance of target agronomic, horticultural and floricultural plants and plant cuttings. The method involves applying to or exposing a plant and/or plant cutting an effective amount of at least one of the hereinbefore described compositions which contains at least one floral scent precursor which is capable of modifying the emission of a floral scent from a plant or plant cutting. If the composition is to be applied to a plant cutting, it may also optionally also contain a nutrient source as described previously.

Monoterpenes are known to play a role in the natural defense systems of plants against pests and pathogens (see Francke, W. in Muller, P. M. and Lamparsky, D., eds., *Perfumes: Art, Science and Technology*, Elsevier Applied Science, New York, N.Y., 61–99 (1991); Harborne, J. B., in Harborne, J. B. and Tomas-Barberan, F. A., eds., *Ecological Chemistry and Biochemistry of Plant Terpenoids*, Clarendon Press, Oxford, 399–426 (1991); Gershenzon, J and Croteau, R in Rosenthal, G. A. and Berenbaum, M. R., eds., *Herbivores: Their Interactions with Secondary Plant Metabolites*, Academic Press, San Diego, 168–220 (1991)).

Thereupon, the compositions described herein can be used in a method to increase the levels of pest and pathogen resistance in agronomic, horticultural and floricultural crops. For example, a composition containing a floral scent precursor, such as benzoic acid or a functional analog thereof, may be applied to a field, greenhouse or orchard in order to induce the production of monoterpenes having defense properties. Such increased levels of pest and pathogen resistance in targeted crops are of obvious economic benefit. Furthermore, monoterpene production can be genetically engineered into a target crop species. Again, using benzoic acid as an example, in a target crop into which monoterpene production has been genetically engineered, activation of the pathway by benzoic acid application(s) can be considered in order to provide transgene-mediated resistance through elevated levels of monoterpenoid production.

In yet another embodiment, the present invention relates to methods for converting an ornamental plant species or particular varieties within a cultivated species that are typically not known or considered to be fragrant, into floral scent-emitting plants. The method involves applying to or exposing said plant or plant cutting to an effective amount of at least one of the hereinbefore described compositions which contains at least one floral scent precursor which is capable of modifying the emission of a floral scent from a plant or plant cutting. If the composition is to be applied to a plant cutting, it may also optionally contain a nutrient source as described previously.

For example, the application of a composition described herein containing an effective amount of at least one floral scent precursor can be used to activate the necessary biosynthetic pathways in plants and plant cuttings used in floral scent production, thus resulting in the increased biosynthesis (production) and/or emission of a floral scent.

In yet another embodiment, the compositions described for used in connection with the hereinbefore described methods can also be used in conjunction with a range of methods for genetically engineering plants. For example, the gene encoding benzoic acid methyltransferase (for methylbenzoate production) can be introduced into and expressed in a non-fragrant ornamental plant species. By supplying a composition containing benzoic acid to the transgenic plant, the benzoic acid can be enzymatically converted to the volatile floral scent, methylbenzoate, thus providing a pleasant fragrance. An analogous approach can be used for enhancing the flavors and aromas of fruits and vegetables by adding novel floral scent components through plant genetic engineering strategies.

In another example, there may be particular plant species which have been identified as being especially useful and beneficial for in planta production of a valuable fragrance or flavor component, but which exhibit a crippling genetic and/or biochemical flaw (such as, an inefficient floral scent biosynthetic enzyme with inferior enzyme kinetics) which excludes them from further commercial consideration. A genetic engineering strategy can be employed which permits the expression of a transgene which encodes a more efficient biosynthetic enzyme with superior kinetic parameters. This biosynthetic enzyme would be capable of being activated by benzoic acid or a benzoic acid-associated signal (or other floral scent precursors).

In yet another example, regulatory regions of the floral scent biosynthetic genes might contain DNA sequence elements which are involved in the molecular sensing of a benzoic acid-induced signal molecule. Therefore, these regulatory regions could be considered to be chemically-regulatable, and could control gene expression in a chemically-dependent manner. The chemically-regulatable region would be operably linked to a gene of interest for controlled expression of the desired protein. Thus, a chemically-inducible transgene expression system which is controlled by the application of a floral scent precursor such as benzoic acid can be developed.

By way of example, and not of limitation, examples of the present invention shall now be given.

EXAMPLE 1

Phenylalanine and Benzoic Acid as Floral Scent Precursors for Methylbenzoate

Although methylbenzoate has been reported in the floral scent of greater than 30 different species, the immediate biochemical step leading to its synthesis has not been previously elucidated. The inventors hypothesized that methylbenzoate could be synthesized by enzymatic methylation of benzoic acid with S-adenosyl-L-methionine (hereinafter "SAM") as the methyl group donor, in a reaction analogous to the synthesis of methylsalicylate from SAM and salicylic acid. Indeed, crude extracts prepared from different parts of snapdragon flowers were found to contain an enzymatic activity which was able to convert benzoic acid to methylbenzoate in the presence of SAM. This protein was termed benzoic acid methyl transferase (hereinafter "BAMT").

Despite this evidence, it was known to the inventors found that crude extracts can sometimes introduce artifacts that can complicate the interpretations of the results obtained. To demonstrate that benzoic acid was indeed the in planta substrate for methylbenzoate, the following experiment was performed. Ten lower lobes of snapdragon flowers (variety Maryland True Pink, PanAmerican Seed Company, West Chicago, Ill.) were excised from the rest of the flower. Two microliters of $^{14}$C-benzoic acid (500 nanocuries, or nCi) were pipetted onto the cut edge of the lower lobes. At this time, the lobes were allowed to sit for 10 minutes to permit uptake of the radiolabeled benzoic acid. The lobes were placed cut edge down on wet filter paper and the headspace collected over the course of the next four hours. The columns which trapped the volatiles were changed at 30, 60, 120 and 240 minutes after the start of incubation and eluted with 3 mls of hexane. The eluate (1.5 mls) was then analyzed in a liquid scintillation counter for the presence and amount of $^{14}$C-methylbenzoate. The identity of $^{14}$C-methylbenzoate was verified by its retention time on a thin-layer chromatography plate. As can be observed below in Table 2a, emission of $^{14}$C-methylbenzoate was first detected within one hour after the start of the incubation period. Between the first and second hours of headspace collection, the amount of methylbenzoate increased significantly. This increase was even more dramatic over the next 2 hours as the amount of methylbenzoate emissions increased over 5-fold (compared to the first 2-hour collections period). These results showed that $^{14}$C-methylbenzoate was rapidly synthesized and emitted from the snapdragon flower after addition of radiolabeled $^{14}$C-benzoic acid. These results strongly support the in vitro enzymatic assay results that benzoic acid is indeed a floral scent precursor to methylbenzoate.

In additional experiments (see Table 2b below), an essentially identical radiolabeled experiment was performed in which $^{14}$C-phenylalanine (220 nCi) was substituted for $^{14}$C-benzoic acid as the radiolabeled floral scent precursor. As was observed previously with $^{14}$C-benzoic acid, the $^{14}$C-phenylalanine was rapidly converted to $^{14}$C-methylbenzoate. Within just 30 minutes after the start of the incubation period, $^{14}$C-methylbenzoate was detected. The amount of $^{14}$C-methylbenzoate increased rapidly during the following three successive collection periods, respectively, (the rate increasing during each successive period). This data demonstrates that phenylalanine is also a floral scent precursor compound for methylbenzoate production in plants. Taken together these results further demonstrate that both phenylalanine and benzoic acid are precursors to methylbenzoate, with benzoic acid being the likely immediate precursor.

TABLE 2a

Conversion of $^{14}$C-Benzoic Acid to $^{14}$C-Methylbenzoate in situ by Snapdragon Petals

| Time (min.) | nCi[1] |
| --- | --- |
| 0 | 0.030 |
| 30 | 0.036 |
| 60 | 0.354 |
| 120 | 2.544 |
| 240 | 13.226 |

[1]nanocuries of $^{14}$C-methylbenzoate from $^{14}$C-benzoic acid

TABLE 2b

Conversion of $^{14}$C-Phenylalanine to $^{14}$C-Methylbenzoate in situ by Snapdragon Petals

| Time (min.) | nCi[1] |
| --- | --- |
| 0 | 0.295 |
| 30 | 0.983 |
| 60 | 1.874 |
| 120 | 5.635 |
| 241 | 25.387 |

[1]nanocuries of $^{14}$C-methylbenzoate from $^{14}$C-phenylalanine

EXAMPLE 2

Benzoic Acid Enhances Floral Scent Emission in Cut Snapdragon Flowers

In accordance with the idea that benzoic acid availability for enzymatic conversion to methylbenzoate might influence floral scent emission by snapdragon flowers, the following experiment was conducted. Volatiles emitted from snapdragon flowers were determined by headspace analysis, as described previously (Raguso and Pichersky, 1995, *Plant Systematics and Evolution* 194:55–67). Collection of floral scent compounds proceeded for a fixed period of time under growth chamber (Conviron, model E8) conditions with 12 hour photoperiod and a 25° C./20° C. (light /dark) temperature cycle. Flowers attached to the plant were enclosed in a polyvinylacetate bag (Reynolds, Inc.) and purified air was pumped over the flower at a flow rate of 250 ml/minute. Existing volatiles were adsorbed on a Porapak Q (80–100 mesh size) (Alltech, Inc.) cartridge, eluted from the cartridge with 3 ml of hexane and concentrated to 60 μl. 10 μl of a 0.03% napthalene solution in hexane were added as an internal standard. Trapped floral scent compounds were analyzed by GC-MS (Finnigan MAT GCQ; injector temperature 230° C., injector volume 1 ml, split ratio 50:1) using a DB-1 nonpolar capillary column (30 m; 0.25 mm internal diameter; 0.25 mm film thickness). Ionization energy was set at 70 eV. Column temperature programming was: 50° C. for 1 minute, then heated to 240° C. at a rate of 10°/minute. The MS was scanned from 41 to 400 AMU (atomic mass units). Simultaneous collections of ambient volatiles were used as controls. Components were first identified through a computer database containing several thousand mass spectra and confirmed by comparison of retention times and mass spectra of authentic standards.

Headspace collection of greenhouse-grown, inflorescence-bearing snapdragons (Maryland True Pink, Pan-American Seed Company, West Chicago, Ill.) was carried out for 24 hours. The snapdragon inflorescence-bearing stems for this experiment were carefully chosen to have a similar number of same-aged flowers. After this period, the inflorescence-bearing stems were placed into each of four different treatments: a) water; b) 5% (w/v) sucrose; c) 0.1 mg/ml benzoic acid; and d) 5% (w/v) sucrose supplemented with 0.1 mg/ml benzoic acid. The sucrose level chosen was based upon the conclusions reached by Ichimura and Hisamatsu (1999, *Journal for the Japanese Society for Horticultural Science*, 68:61–66) that 5% (w/v) sucrose was the optimum sucrose level for maximum vase life of cut snapdragon flowers. Headspace collection was then carried out for 48–120 hours after harvesting, with the floral scent volatiles collected and measured each successive 24-hour period.

As shown below in Table 3, the water-treated control continued to emit 92% of the total volatiles (compared to the pre-harvest level on Day 0) during the initial 24-hour period after harvest (Day 1). This value declined to 68% during the second 24-hour period after harvest (Day 2). When the cut stem incubated in 5% (w/v) sucrose was measured, it was found that these flowers emitted 85% and 48% (of the Day 0 pre-harvest amounts) during the first and second 24-hour periods, respectively, after cutting (Days 1 and 2). When the floral scent emission from the flowers treated with 0.1 mg/ml benzoic acid (BA) was examined, these flowers emitted 120% and 114% of the total volatiles emitted prior to harvest on Days 1 and 2, respectively. As indicated by the data, this rate of floral scent emission is even higher than the amount of floral scent volatiles measured before the stem was harvested, indicating no decrease (like was observed for the water- and sucrose-treated cut flowers) in total floral scent biosynthesis and/or emission, but an actual increase in emission. However, after the initial 48-hour period after harvest (Days 3–5), floral scent emission declined rapidly to amounts only 12–16% of that measured prior to harvesting.

TABLE 3

Exposure of Cut-Snapdragon Flowers to Benzoic Acid Enhances Floral Scent Emission

| Treatment | Day | | | | | |
|---|---|---|---|---|---|---|
| | 0 | 1[1] | 2 | 3 | 4 | 5 |
| Water | 100 | 92[2] | 68 | ND[3] | ND | ND |
| Sucrose | 100 | 85 | 48 | ND | ND | ND |
| BA | 100 | 120 | 114 | 15 | 16 | 12 |
| Sucrose/BA | 100 | 146 | 107 | 66 | 83 | 99 |

[1]Days after harvest
[2]Percentage amount of total floral scent emitted compared to the total floral scent emitted during the 24-hour period prior to harvest (where Day 0 equals 100%)
[3]ND = Not Determined.

When the cut snapdragon flowers exposed to 5% (w/v) sucrose supplemented with 0.1 mg/ml benzoic acid (Sucrose/BA) were measured for their emission level, it was found that emission remained extremely high during the first 48 hours after harvesting, measuring 146% and 107% of pre-harvest (Day 0) levels during the first and second 24-hour periods, respectively. This result is in close agreement with what was observed for the flowers treated with 0.1 mg/ml benzoic acid (BA) alone. However, a dramatic difference was noted for these flowers treated with 5% (w/v) sucrose/0.1 mg/ml benzoic acid in the following three days. It was found that in the 24-hour period between two and three days after harvest (Day 3), these flowers were still emitting 66% of the total volatiles (measured prior to harvest). Even still more dramatically, the emission amounts climbed to 83% and 99% of pre-harvest amounts during the fourth and fifth 24-hour periods after harvest, respectively. That is, the level of floral scent emission 5 days after harvest was still equal to the level of emission measured prior to harvesting. These unexpected results stand in sharp contrast to the floral scent emission levels measured in flowers treated with benzoic acid (BA) alone or sucrose alone.

The results presented above in Table 3 demonstrate that in the initial 24–48 hours after harvesting, that the inflorescence-bearing stem has an adequate nutrient supply since the inclusion of 5% (w/v) sucrose did not substantially affect the emission levels from the sucrose-treated flowers (compare 92% and 68% for the water treatment to 85% and 48% for the 5% (w/v) sucrose treatment). However, it is evident that the benzoic acid had a stimulatory effect (120% and 114% of the pre-harvest level) upon floral scent emission since emission levels were substantially increased relative to the water or sucrose alone treatment. This result indicates that benzoic acid availability is limiting the amount of floral scent emission from the cut snapdragon stems. This is further supported by the data for the cut snapdragon flowers treated with 5% (w/v) sucrose/0.1 mg/ml benzoic acid since the emission from these flowers was also stimulated to an amount exceeding pre-harvest levels (146% and 107% on days 1 and 2, respectively). Taken together, the treatments containing benzoic acid convincingly enhance floral scent emission during the initial 1–5 days after harvesting.

This data further demonstrates that both benzoic acid and sucrose must be present in the treatment in order to support and maintain maximal floral scent emission levels in cut snapdragon flowers. In the absence of sucrose, the 0.1 mg/ml benzoic acid-treated flowers emit less than 20% of the pre-harvest amounts of volatiles on Days 3–5. Though not measured here in this particular Example, after 48 hours of sucrose treatment (by which time it had already declined to approximately 48%), but as demonstrated in another Example described herein with cut petunia (See Example 4), the sucrose-treated flowers continue to decline in their emission levels on days 3–5, much like the benzoic acid-treated flowers. However, in the presence of both an adequate nutrient supply (in this case 5% (w/v) sucrose) and an adequate floral scent precursor supply (in this case, 0.1 mg/ml benzoic acid), the snapdragon flowers are able to continue emitting substantially higher amounts of floral scent throughout the duration of the experiment. This result demonstrates that for maximal emission of floral scent volatiles from cut snapdragon flowers, a dual component system that includes both a nutrient source (e.g., a plant food like sucrose or another carbohydrate) and a floral scent precursor (e.g., benzoic acid) is required. In the absence of plant nutrients, the cut flowers gradually exhaust or deplete their energy reserves and are unable to sustain the biosynthesis and/or emission of the floral scent volatiles, an apparently energy-intensive process. In the absence of a substrate like benzoic acid, the cut flowers may or may not have the necessary energy to produce and emit floral scent, but may lack or have insufficient quantities of substrate (due to depleted benzoic acid pools) with which to produce floral scent.

EXAMPLE 3

Benzoic Acid as a Primary Determinant of Floral Scent Emission in Snapdragon

The results and conclusions described in Example 2 demonstrate that benzoic acid availability is a primary determinant in the floral scent emission levels in cut (i.e., harvested) snapdragon stems. With this in mind, these results suggested to the inventors that benzoic acid might also influence floral scent emission patterns in intact (i.e., not harvested) snapdragon plants. To test this hypothesis, endogenous pools of benzoic acid in petal tissue during flower development were measured. At the same time, BAMT activity and methylbenzoate emission were also monitored.

Benzoic acid (hereinafter "BA") was extracted using supercritical carbon dioxide extraction at 414 bar and 40EC using SFX-210 Extractor outfitted with a 2600 pump and a temperature controlled variable restrictor (ISCO Inc., Lincoln, Nebr.) (McHugh and Krukonis, 1994, in Supercritical Fluid Extraction, Boston, Mass., Butterworth-Heinemann). Four grams of petal tissue (from the upper and lower lobes) at different stages of flower development were extracted with 440 ml $CO_2$ at a flow rate of approximately 7 ml/minute. Extracts were collected in a test tube filled with 4 ml of methanol, filtered through 0.2 µm pore-size nylon filters (Nalgene, Rochester, N.Y.) to eliminate insoluble debris and concentrated to 150 µl. The samples (25 µl) were injected and the compounds were separated on a C18 reverse phase high Performance Liquid Chromatography (hereinafter "HPLC") column (Hibar Ec Cartridge containing Merk Lichrosorb RP-18 10-µm C18 reverse phase packing, 4.6 mm×25 cm (Alltech Associates, Deerfield, Ill.)) maintained at 20° C. Benzoic acid was separated during a 15 minute gradient of methanol (25–70%) at a flow rate of 1.2 ml/minute maintained by HPLC pump (Varian 9012). HPLC grade water was adjusted to pH 3 with phosphoric acid (Graham, 1991, *Plant Physiology* 95:584–593). Benzoic acid was detected and quantified by UV absorption at 210 nm (Varian 9050, variable wavelength UV-VIS detector). Under these conditions, retention time for benzoic acid was 8.6 minutes and the limit of detection was 6 µg/ml of BA (0.5 µg per injection). Standard solutions containing 6 µg/ml–120 µg/ml of authentic BA were used to prepare a standard curve. All data were corrected for BA recovery, using internally spiked samples.

Benzoic acid in plant extracts was verified by mass spectral analysis and also confirmed by its co-elution with authentic standard using HPLC. For GC-MS analysis, BA peak was collected from the HPLC, air dried, and resuspended in 20 µl of acetone. BA was derivatized by adding 100 µl of Bis(trimethylsilyl)trifluoroacetamide (BSTFA) which makes a trimethylsilyl ester of BA. After incubation for 10 minutes at room temperature, the reaction mixture was heated in the GC-oven at 50° C. for 5 minutes. The derivatized sample was analyzed by Finnigan MAT GCQ mass spectrometer using a DB-1 nonpolar-capillary column. Ionization energy was set at 70 eV. Column temperature programming was: 50° C. for 0.1 minutes, then heated to 240° C. at a rate of 10° per minute. Obtained GC-MS spectrum was compared with authentic BA derivatized in the same way.

A substantial pool of benzoic acid was found in petal tissue, and the size of this pool changed during development (see Table 4 below). The highest content of benzoic acid (19.6 µg/g fresh weight) was found on day 2 after anthesis when the emission of methylbenzoate and the activity of BAMT are relatively low (approximately 30% of maximum). The petal concentration of benzoic acid declined in a way (approximately 2-fold) that coincided with the increasing amount of BAMT activity and emission of methylbenzoate until day 7 after anthesis. After that time, the emission of methylbenzoate beings to decline, precipitously so after day 8. Meanwhile, the amount of benzoic acid continues its descent, especially after day 7, whereas the amount BAMT activity remained relatively high (still at nearly 50% of maximum on day 12). Thus, the low emission of methylbenzoate in older flowers (only approximately 10–15% of maximum) could be due to the limited amount of benzoic acid (also only at approximately 10–15% of maximum).

TABLE 4

Developmental Regulation of Benzoic Acid Content, BAMT Activity and Methylbenzoate Emission in Snapdragon Flowers

| Time postanthesis | Benzoic Acid | BAMT Activity | Methylbenzoate emission |
|---|---|---|---|
| Bud | 5.2[1] | 23[2] | 0.0[3] |
| 1[4] | 2.8 | 129 | 1.7 |
| 2 | 19.6 | 171 | 15.4 |
| 3 | 15.2 | 250 | 34.6 |
| 4 | 12.1 | 369 | 42.3 |
| 5 | 11.8 | 409 | 52.0 |
| 6 | 8.3 | 393 | 55.7 |
| 7 | 9.2 | 405 | 55.8 |
| 8 | 7.0 | 407 | 47.8 |
| 9 | 4.9 | 380 | 29.8 |
| 10 | 4.4 | 370 | 6.6 |
| 11 | 2.0 | 303 | 8.2 |
| 12 | 2.9 | 211 | 5.1 |

[1]µg/g fresh weight petal tissue
[2]pkat/flower
[3]µg/flower/24 hours
[4]days

The emission of methylbenzoate declines toward the end of the life span of the flower (9–12 days after anthesis) whereas BAMT activity remains relatively high (46% of the maximum level). Interestingly, BAMT activity in 3- and 12-day-old flowers is similar, indicating that the protein in old flowers is capable of producing the same amount of methylbenzoate as those of 3-day-old flowers. However, the amount of methylbenzoate emission is almost seven times higher in young flowers than in old ones. The finding that the amount of benzoic acid in petal tissue of 12-day-old flowers is only one-fifth that of 3-day-old flowers indicates that the amount of substrate present is a limiting factor. The low amount of benzoic acid in old flower petals may indicate that the earlier biochemical steps in the pathway are blocked as the flower ages or that synthesized benzoic acid is required for some other processes in the cells. Plotting the emission of methylbenzoate from snapdragon flowers against predicted production of methylbenzoate gives a correlation coefficient for linear regression analysis of 0.95, indicating that production of methylbenzoate is regulated by the amount of benzoic acid and the amount of BAMT protein, with the latter being regulated at the transcriptional level.

The data demonstrates that the sizes of the benzoic acid pools in upper and lower petal lobes are indeed developmentally regulated. It should be noted that even in younger-aged flowers, when benzoic acid pool sizes are at or near maximum sizes, it is possible that benzoic acid availability may be limiting the amount of floral scent emission even at this developmental stage. If so, exogenously-added benzoic acid would increase pool sizes to larger-than-normal amounts, thus increasing methylbenzoate biosynthesis and/or emission. This is supported by the results shown in Example 2 where benzoic acid exposure (in the absence or presence of sucrose) stimulated floral scent emission, including emission of methylbenzoate (see Example 5 below), early in the experiment with relatively young-aged flowers.

EXAMPLE 4

Benzoic Acid Enhances Floral Scent Emission in Petunia

Having demonstrated that benzoic acid content could affect floral scent emission in both intact and cut snapdragon inflorescence-bearing stems, the inventors sought to determine whether the floral scent emission patterns of other flowers could be manipulated in a similar manner. The petunia variety called 'Mitchell' is an older, non-commercial (i.e., research use only) cultivar (generally available from academic research institutions) that was previously known to emit floral scent, especially during the evening hours. Gas chromatographic-mass spectrometry analysis revealed that this floral scent was composed almost exclusively of methylbenzoate. With this identification of floral scent in hand, the uptake experiments carried out in Example 2 on cut snapdragon stems were repeated with inflorescence-bearing Mitchell petunia cuttings.

Headspace collection was performed on two intact flowers for a 24-hour period prior to harvest to measure the amount of methylbenzoate emitted. This methylbenzoate emission was measured by GC-MS and these values set at 100%. The two inflorescence-bearing stems were harvested and immediately were placed into a vessel containing 5% (w/v) sucrose or a vessel containing 5% (w/v) sucrose supplemented with 0.1 mg/ml benzoic acid. Headspace collection was carried out as described in Example 2 on the cuttings for five 24-hour periods after harvesting. During the fifth 24-hour period, the flowers on both cuttings eventually senesced and collapsed.

As shown below in Table 5, during the first two 24-hour periods after harvest (Days 1 and 2), the 5% (w/v) sucrose-treated flower emitted between 62% and 76% of the amount of methylbenzoate measured prior to harvest (Day 0). In contrast, the flower treated with 5% (w/v) sucrose/0.1 mg/ml benzoic acid (Sucrose/BA) emitted between 86% and 93% of the level of methylbenzoate measured prior to harvest. The differences in methylbenzoate emission amounts grew even more striking in the next two 24-hour periods of headspace collection. During the third 24-hour period of collection, the 5% (w/v) sucrose-treated flower emitted less than 50% of the methylbenzoate emitted prior to harvest. In sharp contrast, the 5% (w/v) sucrose/0.1 mg/ml benzoic acid-treated flower was now emitting more methylbenzoate (105%) than before harvest. Similarly, on Day 4 of headspace collection, emission from the 5% (w/v) sucrose-treated flower had continued to decline, now emitting slightly more than 30% of the original level of methylbenzoate emitted from the flower. In even sharper contrast than found on Day 3, the 5% (w/v) sucrose/0.1 mg/ml benzoic acid-treated flower was now emitting even greater amounts (123%) than at the time prior to harvest. That is, the 5% (w/v) sucrose/0.1 mg/ml benzoic-treated flower was emitting a nearly 4-fold greater amount of methylbenzoate than the 5% (w/v) sucrose-treated flower alone. During Day 5, both flowers eventually senesced and collapsed, causing a precipitous decline in methylbenzoate emission in both flowers. However, the amount of emission in the 5% (w/v) sucrose/0.1 mg/ml benzoic acid-treated flower was still nearly 2-fold higher when compared to the 5% (w/v) sucrose-treated flower, even at the time of flower collapse.

TABLE 5

Benzoic Acid Stimulates Methylbenzoate Emission in Petunia Cuttings

| Treatment | Day[1] | | | | | |
| --- | --- | --- | --- | --- | --- | --- |
|  | 0 | 1 | 2 | 3 | 4 | 5 |
| Sucrose | 100 | 62[2] | 76 | 48 | 33 | 23 |
| Sucrose/BA | 100 | 86 | 93 | 105 | 123 | 40 |

[1]Days after harvest
[2]Percentage amount of methylbenzoate emitted compared to the total methylbenzoate emitted during the 24-hour period prior to harvest (where Day 0 equals 100%)

The observations and results described in this Example provide a number of useful insights. First, the results in this Example are very similar to the results obtained with 5% (w/v) sucrose/0.1 mg/ml benzoic acid-treated cut snapdragon flowers. In both cut snapdragon and petunia flowers treated with 5% (w/v) sucrose/0.1 mg/ml benzoic acid, there is an initial decline in the amount of total floral scent emitted from the flowers of which lasts for approximately two days after harvest. After this period, the flowers of both species begin to increase the amount of floral scent emitted so that by the end of the of headspace collection period (a day when the flowers are still alive and healthy), both flowers are emitting more floral scent than when the flower was still attached to the plant. In contrast, the flowers treated with 5% (w/v) sucrose are only able to emit a fraction of the floral scent volatiles found for the 5% (w/v) sucrose/0.1 mg/ml benzoic acid-treated flowers.

Additionally, as was observed with snapdragon (see Example 5 below), the 5% (w/v) sucrose-treated petunia cutting emits considerable, albeit reduced amounts of methylbenzoate, during the first 48 hours after harvest. However, in subsequent days, methylbenzoate emissions declined precipitously. In petunia, methylbenzoate emission declined by more than 2-fold over the next two 24-hour collection periods. Like snapdragon, these results are consistent with the idea that the rapidly dwindling pool of benzoic acid for enzymatic conversion to methylbenzoate limits the biosynthesis and emission from the flower. As reported in Example 3, aging snapdragon flowers have greatly reduced benzoic acid levels which limits methylbenzoate biosynthesis and emission. It should be noted that the two petunia cuttings chosen for this Example contained flowers of the approximate same age (see Table 5 that shows both flowers senesced and collapsed at the same time), and thus the differences found in floral scent emission seemed unlikely to be related to flower age. That is, it seems unlikely that the observed emission differences can be attributed to developmentally-regulated levels of BAMT protein and/or enzymatic activity in the petunia flowers.

EXAMPLE 5

Benzoic Acid Enhances Floral Scent Emission of Non-methylbenzoate-related Components in Snapdragon Flowers In this Example, a closer examination of the data generated in Example 2 (see Table 3 and Table 6 below) reveals that the total floral scent emitted by the Maryland True Pink snapdragon flowers is actually comprised of three different volatile compounds (in order of decreasing relative amounts), ocimene, methylbenzoate and myrcene. Ocimene, the major floral scent emitted by Maryland True Pink, and myrcene, the least abundant floral scent, are related compounds derived from the monoterpenoid pathway. As discussed earlier, monoterpenes are a broad class of low molecular weight $C_{10}$ compounds that are synthesized in the plastid of the plant cell. All monoterpene synthases are thought to utilize GPP (GPP is derived from DMAPP/IPP) as the substrate for the biosynthesis of both cyclic and acyclic monoterpenoids. By comparison and has already been discussed, methylbenzoate is likely synthesized in the cytosolic compartment by methylation of benzoic acid. At this time, there is no known overlap or intersection between these two metabolic pathways, the monoterpenoid and phenylpropanoid pathways, in the plant cell as they are separated not only by substrate utilization but also by compartmentalization within the cell. However, the results shown below in Table 6 clearly demonstrate that exposure to benzoic acid enhances emission of both phenylpropanoid-type (e.g., methylbenzoate) and monoterpenoid-type (e.g., ocimene and myrcene) floral scent volatiles in cut snapdragon flowers.

TABLE 6

Benzoic Acid Modifies the Floral Scent Emissions of Methylbenzoate and the Monoterpenoids, Ocimene and Myrcene, in Cut Snapdragon Flowers

| Treatment | Volatile | Day | | | | | |
| --- | --- | --- | --- | --- | --- | --- | --- |
| | | 0 | 1[1] | 2 | 3 | 4 | 5 |
| Water | Ocimene | 100 | 106[2] | 73 | ND[3] | ND | ND |
| | Myrcene | 100 | 119 | 86 | ND | ND | ND |
| | Methylbenzoate | 100 | 53 | 44 | ND | ND | ND |
| Sucrose | Ocimene | 100 | 88 | 58 | ND | ND | ND |
| | Myrcene | 100 | 78 | 55 | ND | ND | ND |
| | Methylbenzoate | 100 | 78 | 30 | ND | ND | ND |
| BA | Ocimene | 100 | 139 | 122 | 20 | 18 | 18 |
| | Myrcene | 100 | 158 | 142 | 23 | 26 | 18 |
| | Methylbenzoate | 100 | 84 | 91 | 8 | 4 | 3 |

TABLE 6-continued

Benzoic Acid Modifies the Floral Scent Emissions of Methylbenzoate and the Monoterpenoids, Ocimene and Myrcene, in Cut Snapdragon Flowers

| Treatment | Volatile | Day | | | | | |
| --- | --- | --- | --- | --- | --- | --- | --- |
| | | 0 | 1[1] | 2 | 3 | 4 | 5 |
| Sucrose/ | Ocimene | 100 | 154 | 116 | 79 | 106 | 125 |
| BA | Myrcene | 100 | 135 | 115 | 67 | 89 | 89 |
| | Methylbenzoate | 100 | 135 | 88 | 46 | 46 | 63 |

[1]Days after harvest
[2]Percentage amount of each floral scent emitted compared to the amount of each floral scent emitted during the 24-hour period prior to harvest (where Day 0 equals 100%)
[3]ND = Not Determined.

In the experiment described in Example 2, when only water was present, the monoterpenoids are emitted at or above their pre-harvest amounts (ocimene at 106% and myrcene at 119%) during the first 24-hour period after the cutting was harvested (Day 1). In contrast, the methylbenzoate levels dropped to 53% of pre-harvest levels. During the second 24-hour period (Day 2), ocimene and myrcene declined to 73% and 86% of pre-harvest levels (Day 0), respectively, while methylbenzoate declined even further to 44% of the pre-harvest amount.

In the presence of 0.1 mg/ml benzoic acid (BA), during the initial 24 hours after harvest (Day 1), the methylbenzoate levels remained at 84% of pre-harvest levels (compared to 53% for the water-treated). Moreover, the emitted amount of this volatile ester even increased (up to 91% of pre-harvest levels) during the second 24-hour period (Day 2) (compared to 44% for the water-treated on Day 2). This is more than 2-fold higher than that observed for water-treated flowers. This demonstrates that the exogenously-supplied benzoic acid is able to support and maintain the pre-harvest levels of methylbenzoate biosynthesis and emission. However, it was unexpectedly discovered that the emission levels of the monoterpenes, ocimene and myrcene were also dramatically elevated compared to pre-harvest levels. With respect to ocimene, the emission levels were found to be at 139% and 122% of pre-harvest amounts on the first and second 24-hour headspace collection periods (Days 1 and 2) after harvesting, respectively. Similarly, for myrcene, the emission levels were measured to be at 158% and 142% of pre-harvest, respectively amounts during the same time period. These values for ocimene and myrcene are significantly higher than were noted for the cut snapdragon flowers treated with water only (See Table 6). This enhancement in monoterpenoid emission by exposure to benzoic acid was unanticipated since, as discussed above, benzoic acid is not thought to have any direct or indirect role in monoterpenoid biosynthesis and/or emission. In the remaining days (Days 3–5), the emission amounts declined for all three floral scent volatiles, but it should be noted that the monoterpene emission amounts did not decline as much (stabilizing at approximately 20–25% of pre-harvest levels) as found for methylbenzoate (which declined to less than 5% of the pre-harvest amount).

When the results of the 5% (w/v) sucrose-treated flowers are considered, observations similar to those made for the water-treated flowers were noted. After the first two 24-hour periods after harvest (Days 1 and 2), methylbenzoate emission levels declined to 78% and 30% of pre-harvest amounts, respectively. Once again, the emission patterns of the two monoterpenes were essentially identical. The emission levels of ocimene declined to 88% and 58% of pre-harvest levels one and two days after harvest, respectively. Likewise, myrcene emission levels declined to 78% and 55% of pre-harvest levels one and two days after harvest, respectively. Thus, for both the water and 5% (w/v) sucrose treatments, the floral scent emission profiles were essentially identical as the overall total levels of floral scent emission declined, including for each of the individual floral scent volatiles measured. This clearly differs from the 0.1 mg/ml benzoic acid-treated flower as all floral scent volatiles measured were at or above pre-harvest levels during the first two days after harvest.

The most striking results were found in the cut flower stems treated with 5% (w/v) sucrose/0.1 mg/ml benzoic acid. In the first 24-hour period after harvest (Day 1), the levels of methylbenzoate increased to 135% of pre-harvest amounts before declining to 88% during the second 24-hour period. In the three subsequent days of headspace collection, the levels remained essentially steady at 46% on Days 3 and 4 before rebounding to 63% of pre-harvest amounts on Day 5. With respect to the two monoterpenes, ocimene emission levels increased to 154% of pre-harvest amounts on the first day after harvest. This was followed by slight decreases on Days 2 (116%) and 3 (79%) after harvest. However, on Days 4 and 5, the ocimene levels rebounded to 106% and 125% of pre-harvest levels, respectively. Upon examination of myrcene emission levels, the same floral scent emission pattern that was noted for ocimene was observed. On Day 1 after harvest, the myrcene emission levels climbed to 135% of pre-harvest amounts before declining to 115% on Day 2. This was followed by a decline to 67% on Day 3 before rebounding to approximately 89% on both Days 4 and 5.

To summarize, at the outset of this experiment, the monoterpene portion of the total floral scent emitted was measured to constitute approximately 64% of the floral scent emitted by the intact (pre-harvest) inflorescence-bearing stem. By the end of the 5-day treatment period, the monoterpenes now represented 74% of the total floral scent emitted for the 5% (w/v) sucrose/0.1 mg/ml benzoic-acid treated flowers. This result was unexpected as the inventors would have expected that if benzoic acid were functioning exclusively as a substrate for enzymatic conversion to methylbenzoate, then methylbenzoate should have become a more predominant component in the total floral scent emitted from snapdragon. It was not anticipated that exposure to benzoic acid would act as a general or universal enhancer of floral scent emission from cut snapdragon flowers.

While not wishing to be bound by any theory or hypothesis, the present inventors believe that benzoic acid may be acting in a manner other than simply as a substrate for conversion to methylbenzoate. One hypothesis is that benzoic acid may be acting as a general inducer of floral scent biosynthesis and emission in plants. A closely-related molecule, salicylic acid, is directly involved as a signaling molecule in the induction of the systemic acquired resistance (SAR) response in plants. Salicylic acid is a potent, phloem-mobile inducer of this complex pathway that results in global increases of defense-related gene expression patterns. The inventors hypothesize that benzoic acid may act as a similar inducer of floral scent biosynthetic genes and enzymes. Presently, it should be noted that benzoic acid has already been found to induce the transcription of a defense-related (but not a floral scent biosynthetic) gene, IS10a, after exposure of tobacco cells to 200–400 mM benzoic acid (equivalent to 0.025–0.05 mg/ml, or about a 2- to 4-fold lower rate than used in these experiments)) (Horvath and Chua, 1996, *Plant Molecular Biology* 31:1061–1072).

A second equally plausible hypothesis is that benzoic acid can be acting as a compound that affects membrane permeability. Benzoic acid has already been described as an agent that is able to increase the membrane permeability of plant cells. For example, Baziramakenga et al. (1995, *Journal of Chemical Ecology* 21:1271–1285) demonstrated that when intact root systems of soybean seedlings were exposed to benzoic acid or cinnamic acid, a rapid increase in electrolyte leakage was observed. They also found that these chemicals induced lipid peroxidation, which resulted from free radical formation in plasma membranes, inhibition of catalase and peroxidase activities, and sulfhydryl group depletion. They concluded that oxidation or cross-linking of plasma membrane sulfhydryl groups is the first mode of action of both compounds. Their final conclusion was that both these compounds decreased the integrity of the cell membranes.

Stirnberg (1995, *Planta* 196:706–71 1) measured the membrane potential of hypocotyl cells in light-grown, intact *Nicotiana plumbaginifolia* seedlings. He reported that exposure to 1 mM benzoic acid (or approximately 0.125 mg/ml) induced rapid and weak hyperpolarization, providing further evidence for benzoic acid's effect on plasma membranes.

The inventors further hypothesize that the benzoic acid taken up through the cut end of the stems is transported to the flower petals. In snapdragon, production of the floral volatiles is limited mostly to the upper and lower lobes of the petals. Even more restrictive, production and emission of methylbenzoate occurs almost exclusively from the epidermal cells in the upper and lower lobes of the petals. Given the absence of specialized secretory glands for release of floral volatiles from the epidermal cells, the inventors believe that the highly-volatile floral scent molecules, of low-molecular weight and low solubility in an aqueous environment, somehow move to the plasma membrane. At that point, the floral scent volatiles move through the membrane, past the cell wall, and quickly evaporate into the atmosphere. If the integrity of the plasma membrane has been compromised by benzoic acid-induced damage, the floral scent molecules may have an easier passage though the membrane and would be expected to volatilize at a greater rate, resulting in increased floral scent emissions (and essentially irrespective of the identity of the volatiles).

EXAMPLE 6

Benzoic Acid Enhances Floral Scent Emission in Cold-treated Snapdragons

In commercial cut flower production areas, a ubiquitous and absolutely essential growing practice is to harvest the flowers and transport them immediately to a refrigerated area to remove the 'field heat' from the flower bunches. Over the years, it has become firmly established that maintaining cut flowers under refrigerated conditions is crucial to maintaining the freshness of the flower-bearing cut stem. In fact, the cut flowers remain at refrigerated temperatures throughout the packaging, shipping, and distribution phases of the product. It is not until the consumer purchases the cut flowers at the retail outlet that the flowers are finally restored to ambient temperature on a full-time basis. Thus, this practice is designed exclusively to maximize the vase life of the cut flower for the end user (i.e., the consumer).

At the same time, current commercial cut flower production areas are often located overseas now due to optimum year-round growing conditions and a plentiful source of inexpensive labor. This demands that flowers be packaged and shipped for long-distance travel, which often means that the flowers are maintained under conditions of constant darkness (or near-darkness) for extended periods of time. The last two observations taken together indicate that freshly-harvested flowers, immediately after harvest, may be subjected to extended periods of refrigerated temperatures and darkness. This situation raised the obvious question as to what effect climactic conditions might have upon floral scent emission, and if they do, what effect might exposure of such-treated cut flowers to floral scent precursors have upon floral scent emission.

The effect of temperature on floral scent emission has generally received extremely little attention, but it has been shown that temperature has a strong effect on the quantity of floral scent. For example, total emission of floral scent from intact (not excised) *Trifolium repens* L. flowers was 58% higher at 20° C. than at 10° C. and all compounds of floral scent were affected by the change in temperature (Jakobsen and Olsen, 1994, *Planta* 192:365–371). From these studies, it was not clear if the decrease in emission was due solely to the lesser volatility of these compounds at the lower temperature, or if it was also due to biological processes, including decreased biosynthesis. These studies also did not reveal whether the emission rate could be fully restored by returning the flowers to an ambient temperature.

Similarly, the effect of light on floral scent emission has not received a sufficient amount of attention. In the same studies by Jakobsen and Olsen (1994, *Planta* 192:365–371), they demonstrated that higher emission was noted at high irradiance. However, they noted, as had other investigators previously, that the influence of irradiance may be in part a temperature effect. High irradiance can cause the temperature to rise in the petal tissue, thus increasing emissions primarily through temperature, and not light quantity. Moreover, they demonstrated further that extended periods of darkness (4 days) significantly reduced fragrance emission, which was apparently only partially restored when returned to the light.

Anecdotal stories shared amongst commercial cut flower growers have suggested that extended periods of darkness and/or cold treatment after harvest might be partially responsible for impacting the ability of flowers to emit scent at all or, at best, dramatically reduced levels of floral scent. Snapdragons are a valuable commercially-grown cut flower which can be subjected to extended periods of darkness and refrigerated temperatures following harvest. Therefore, it was not known to the inventors whether these climactic conditions would have any adverse effects upon floral scent emission from cut snapdragon flowers. It is known in the art that maximal emission of floral scent from intact snapdragon plants occurs during the daylight hours; the effects of long-term periods of darkness on floral scent emission from snapdragon flowers were unknown. Thereupon, if the darkness and/or cold treatment were indeed detrimental to floral scent production and/or emission from cut snapdragon flowers, then the inventors were interested in determining whether the sucrose/benzoic acid treatment would overcome this adverse effect and enable us to enhance floral scent emission.

To test the effects of an extended period of both a refrigerated temperature and darkness on floral scent emission from cut snapdragon flowers, and to determine whether the benzoic acid could maintain or enhance floral scent emission in such-treated snapdragon stems, the following experiment was performed. Inflorescence-bearing snapdragon stems were harvested and incubated in water for 48 hours at 4° C. in darkness (to simulate post-harvest conditions at a commercial grower's facility and during shipping). The stems were then moved to ambient temperature in the light and incubated in either 5% (w/v) sucrose or 5% (w/v) sucrose supplemented with 0.1 mg/ml benzoic acid. The floral scent emission from the flowers was then collected for 5 days, and the total emission compared between the various treatments.

As can be observed below in Table 7, the cut snapdragon flowers that were treated with sucrose alone emitted only 30 units of total floral scent. In sharp contrast, the flowers treated with both sucrose and benzoic acid produced 117 units of floral scent, a nearly 4-fold greater amount of floral scent. Moreover, on the $6^{th}$ day at room temperature (8 days post-harvest), the sucrose-treated flowers had already senesced and collapsed while the sucrose/benzoic acid-treated flowers were still producing as much floral scent (29 units) as they were on Day 2 (28 units) and Day 3 (26 units) at room temperature. This data demonstrates that the sucrose/benzoic acid treatment enhances floral scent biosynthesis and/or emission in cut snapdragon flowers subjected to an extended period of refrigerated temperature and reduced light conditions. Moreover, the sucrose/benzoic acid treatment of such-exposed cut snapdragon flowers also permits a longer period of floral scent emission after being returned to an ambient temperature (compared to the sucrose-treated flowers which had ceased emission, senesced and collapsed). Most conclusively, these results demonstrate that storage of cut snapdragon flowers under an extended period of refrigerated temperatures and/or reduced light conditions can negatively impact floral scent emission, even after the flowers are returned to room temperature. However, the benzoic acid/sucrose treatment was shown to be able to enhance floral scent emission demonstrating that this treatment is able to overcome the biochemical and physiological consequences imposed by these climactic conditions on cut flowers.

TABLE 7

Climatic Conditions of Darkness and/or Cold Temperature Negatively Impact Floral Scent Emission in Cut Snapdragon Flowers, and Exposure to Benzoic Acid Overcomes this Effect

| Treatment | Total Emission |
| --- | --- |
| Sucrose | 30[1] |
| Sucrose/benzoic acid | 117 |

[1]Units of total floral scent

EXAMPLE 7

Benzoic Acid Enhances Floral Scent Emission in Snapdragons Through a Spray Application The experiments described in Examples 2 and 4–6 repeatedly demonstrate that benzoic acid is taken up through the cut end of the stem, and transported to the flower to modify floral scent emission. The inventors were interested in determining whether the plant tissue could be exposed to benzoic acid by alternative methods and modify floral scent emission. Since potted plants like miniature roses, chrysanthemums and carnations can also have value for their floral scent as well as their flower color, the inventors wanted to determine if a direct spray application of benzoic acid to an intact (i.e., not harvested) flowering plant could modify floral scent emission.

In this experiment, a flowering snapdragon plant was selected and the headspace collected for a single 24-hour period. After this time, the inflorescence-bearing stem was sprayed to the point of runoff with a solution of 1 mg/ml benzoic acid. The inventors selected the higher concentration of 1 mg/ml benzoic acid (as compared to 0.1 mg/ml concentration for the uptake experiments described in Examples 2 and 4–6) since the benzoic acid spray was designed to be a single-dose application rather than a continuous application (like would be envisioned in the uptake experiments described in Examples 2 and 4–6). The flowers were allowed to dry and the headspace collected for the next 24 hours. After this time period, the experiment was terminated as the flowers were showing evidence of phytotoxicity due to the higher than normal concentration of benzoic acid. However, during this 24-hour period after spray application of benzoic acid, several interesting observations were made. First, the emission levels of the monoterpenoids, myrcene and ocimene, both declined. As can be observed below in Table 8, the levels of ocimene and myrcene declined similarly to 58% and 52% of pre-spray levels, respectively. In sharp contrast, the emission level of methylbenzoate increased to 152% of the pre-spray amount. Overall, the total emission amount remained essentially unchanged (98% of the pre-spray amount). So, while there was no quantitative change in the floral scent emitted during this headspace period, there was a significant qualitative change in the composition of the floral scent emission. The net effect of the benzoic acid spray application was to decrease the contribution of the two monoterpenes to the overall floral scent by almost 2-fold from 57% (prior to spraying) to 33% (after spraying). This modification in floral scent composition was achieved by decreasing the emission levels of the two monoterpenes accompanied by a concomitant increase in methylbenzoate emission.

TABLE 8

A Spray Application of Benzoic Acid to a Potted Snapdragon Plant Modifies Floral Scent Emission

| Floral Scent Volatile | Pre-Spray | Post-Spray |
| --- | --- | --- |
| Ocimene | 100[1] | 58 |
| Myrcene | 100 | 52 |
| Methylbenzoate | 100 | 152 |
| Total | 100 | 98 |

[1]Percentage amount of each floral scent emitted compared to the floral scent amount emitted during the 24-hour period prior to spraying (where the pre-spray amount equals 100%)

These results demonstrate that floral scent emission can be modified through direct spray applications of a floral scent precursor like benzoic acid. Thus, this experiment establishes a second method for exposing plant tissues to a floral scent precursor compound for the purpose of modifying scent biosynthesis and/or emission. This experiment further supports the results found in Examples 2 and 4–6 that benzoic acid can modify floral scent emissions in flowering plants like petunia and snapdragon. While not wishing to be bound by any theory, the enhancement in methylbenzoate emission may be most likely attributable to the exogenously-supplied substrate which was directly applied to petal epidermal cells, the site of floral scent biosynthesis (i.e., where BAMT activity is localized) and emission.

EXAMPLE 8

Plant Uptake of Other Floral Scent Precursors

To determine whether other floral scent precursors were taken up through the cut end of stems, and whether these compounds were transported in flowers other than snapdragon, the following experiment was performed. Cut inflorescence-bearing stems of snapdragon and lisianthus (*Eustoma*) were placed in were placed into solutions containing a range of concentrations of either salicylic acid (the floral scent precursor compound for methylsalicylate) or benzyl alcohol (the floral scent precursor compound for benzylacetate), and incubated at room temperature for up to 1 week. The inventors anticipated that if these floral scent precursors were taken up, then at the highest concentrations, some phytotoxicity might be noted (as was noted for benzoic acid on snapdragon flowers).

Indeed, within 24 hours, both the snapdragon and lisianthus inflorescence-bearing stems treated with 300 mM benzyl alcohol showed signs of phytotoxicity. In both species, the top sections of the stems furthest from the cut end had weakened such that the inflorescence-bearing region of the stem had collapsed and was now sagging downward from the weight of the flowers. Also, in snapdragon, the leaves, especially lower ones, exhibited severe necrosis. By 48 hours, the necrotic symptoms were more evident throughout the entire snapdragon cutting and the leaf necrosis had begun to appear on the lisianthus leaves as well. Moreover, these same symptoms were beginning to appear in cut stems treated with 30 mM benzyl alcohol. By 5 days, all these symptoms were exaggerated in both cut snapdragon and lisianthus inflorescence-bearing stems. Incubation of the cut stems in the lowest concentrations of benzyl alcohol (0.3 mM and 3 mM) never caused any visible symptoms in either lisianthus or snapdragon.

Regarding salicylic acid, only the highest concentration tested, 0.1 mg/ml, produced any phytotoxic effects. Both flower species exhibited slight leaf necrosis. This was first noticeable in snapdragon within two (2) days after exposure, but was not observed in lisianthus until after 5 days of exposure. The lower concentrations of salicylic acid (0.1, 1, and 10 µg/mL) never produced any phytotoxic symptoms.

Taken together, these observations suggested that both benzyl alcohol and salicylic acid are taken up through the cut ends of the snapdragon and lisianthus stems and transported via the vascular system. Moreover, this occurs in other commercially-important cut flower species like lisianthus. These results provide further evidence for the idea that modification of floral scent biosynthesis and/or emission might be achievable in other cut flower crops as well as with other floral scent precursors.

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made to the composition, operation and arrangement of the method of the present invention described herein without departing from the concept and scope of the invention as defined in the following claims.

What is claimed is:

1. A method of increasing the biosynthesis of at least one fragrant volatile compound emitted from a plant, the method comprising the step of:

applying to a plant to an effective amount of a composition comprising at least one floral scent precursor and a nutrient source, wherein the floral scent precursor increases the biosynthesis of at least one fragrant volatile compound emitted from the plant by inducing or activating floral scent biosynthesis and/or emission.

2. The method of claim 1 wherein the floral scent precursor is benzoic acid, trans-cinnamic acid, benzylalcohol, salicylic acid, geranyl pyrophosphate, farnesyl pyrophosphate, jasmonic acid, eugenol or isoeugenol.

3. The method of claim 1 wherein the plant is a potted plant, a hydroponically-grown plant, a field-grown plant, a greenhouse-grown plant, an in vitro-grown plant, or a plant grown in a bioreactor.

4. The method of claim 1 wherein the emission of at least one fragrant volatile compound from the plant is increased.

5. The method of claim 1 wherein the floral scent precursor is present in the composition in the amount of from about 1 ppm to about 1000 ppm.

6. The method of claim 1 wherein the composition further comprises preservatives, excipients or additives.

7. The method of claim 1 wherein the nutrient source is a carbohydrate.

8. The method of claim 7 wherein the carbohydrate is sucrose, fructose, glucose, galactose or raffinose.

9. The method of claim 1 wherein the nutrient source is present in the amount of about 0.5% to about 10% by weight of the composition.

10. A method of increasing the biosynthesis of at least one fragrant volatile compound emitted from a plant cutting, the method comprising the step of:
applying to a plant cutting to an effective amount of a composition comprising at least one floral scent precursor and a nutrient source, wherein the floral scent precursor increases the biosynthesis of at least one fragrant volatile compound emitted from the cutting by inducing or activating floral scent biosynthesis and/or emission,
and further wherein said plant cutting is subjected to refrigerated conditions from about 2° C. to about 15° C.

11. The method of claim 10 wherein the floral scent precursor is benzoic acid, trans-cinnamic acid, benzylalcohol, salicylic acid, geranyl pyrophosphate, farnesyl pyrophosphate, jasmonic acid, eugenol or isoeugenol.

12. The method of claim 10 wherein the emission of at least one fragrant volatile compound from the cutting is increased.

13. The method of claim 10 wherein the cutting is subjected to reduced light conditions.

14. The method of claim 13 wherein the cutting is subjected to the reduced light conditions for a period of from about 1 hour to about 240 hours.

15. The method of claim 14 wherein the cutting is subjected to the reduced light conditions for a period of from about 12 hours to about 168 hours.

16. The method of claim 10 wherein the floral scent precursor is present in the composition in the amount of from about 1 ppm to about 1000 ppm.

17. The method of claim 10 wherein the composition further comprises preservatives, excipients or additives.

18. The method of claim 10 wherein the nutrient source is a carbohydrate.

19. The method of claim 18 wherein the carbohydrate is sucrose, fructose, glucose, galactose or raffinose.

20. The method of claim 10 wherein the nutrient source is present in the amount of about 0.5% to about 10% by weight of the composition.

21. A method of increasing the emission of at least one floral scent from a plant, the method comprising the step of:
applying to a plant an effective amount of a composition comprising at least one floral scent precursor and a nutrient source, wherein the floral scent precursor modifies increases the emission of a floral scent in a plant by inducing or activating floral scent biosynthesis and/or emission.

22. The method of claim 21 wherein the floral scent precursor is benzoic acid, trans-cinnamic acid, benzylalcohol, salicylic acid, geranyl pyrophosphate, farnesyl pyrophosphate, jasmonic acid, eugenol or isoeugenol.

23. The method of claim 21 wherein the plant is a potted plant, a hydroponically-grown plant, a field-grown plant, a greenhouse-grown plant, an in vitro-grown plant, or a plant grown in a bioreactor.

24. The method of claim 21 wherein the emission of at least one fragrant volatile compound from the plant is increased.

25. The method of claim 21 wherein the composition further comprises preservatives, excipients or additives.

26. The method of claim 21 wherein the nutrient source is a carbohydrate.

27. The method of claim 26 wherein the carbohydrate is sucrose, fructose, glucose, galactose or raffinose.

28. The method of claim 21 wherein the nutrient source is present in the amount of about 0.5% to about 10% by weight of the composition.

29. A method of increasing the emission of at least one floral scent from a plant cutting, the method comprising the step of:
applying to a plant cutting an effective amount of a composition comprising at least one floral scent precursor and a nutrient source, wherein the floral scent precursor increases the emission of a floral scent in a cutting by inducing or activating floral scent biosynthesis and/or emission,
and further wherein said plant cutting is subjected to refrigerated conditions from about 2° C. to about 15° C.

30. The method of claim 29 wherein the floral scent precursor is benzoic acid, trans-cinnamic acid, benzylalcohol, salicylic acid, geranyl pyrophosphate, farnesyl pyrophosphate, jasmonic acid, eugenol or isoeugenol.

31. The method of claim 29 wherein the emission of at least one fragrant volatile compound from the cutting is increased.

32. The method of claim 29 wherein the cutting is subjected to reduced light conditions.

33. The method of claim 32 wherein the cutting is subjected to the reduced light conditions for a period of from about 1 hour to about 240 hours.

34. The method of claim 33 wherein the cutting is subjected to the reduced light conditions for a period of from about 12 hours to about 168 hours.

35. The method of claim 29 wherein the floral scent precursor is present in the composition in the amount of from about 1 ppm to about 1000 ppm.

36. The method of claim 29 wherein the composition further comprises preservatives, excipients or additives.

37. The method of claim 29 wherein the nutrient source is a carbohydrate.

38. A method for attracting a pollinator to a plant, the method comprising the step of:
applying to a plant an effective amount of a composition comprising at least one floral scent precursor and a nutrient source, wherein the floral scent precursor increases the emission of a floral scent from a plant by inducing or activating floral scent biosynthesis and/or emission, wherein the increased emission of said floral scent from the plant is sufficient to attract at least one pollinator to said plant.

39. The method of claim 38 wherein the pollinator is a bee or moth.

40. The method of claim 38 wherein the floral scent precursor is benzoic acid, trans-cinnamic acid, benzylalcohol, salicylic acid, geranyl pyrophosphate, farnesyl pyrophosphate, jasmonic acid, eugenol or isoeugenol.

41. The method of claim 38 wherein the floral scent precursor is present in the composition in the amount of from about 1 ppm to about 1000 ppm.

42. The method of claim 38 wherein the composition further comprises preservatives, excipients or additives.

43. The method of claim 38 wherein the nutrient source is a carbohydrate.

44. The method of claim 43 wherein the carbohydrate is sucrose, fructose, glucose, galactose or raffinose.

45. The method of claim 38 wherein the nutrient source is present in the amount of about 0.5% to about 10% by weight of the composition.

46. A method for attracting a plant pest to a plant, the method comprising the step of:
applying to a plant an effective amount of a composition comprising at least one floral scent precursor and a nutrient source, wherein the floral scent precursor increases the emission of a floral scent from a plant by inducing or activating floral scent biosynthesis and/or emission, wherein the increased emission of said floral scent from the plant is sufficient to attract at least one plant pest to said plant.

47. The method of claim 46 wherein the plant pest is an insect.

48. The method of claim 46 wherein the floral scent precursor is benzoic acid, trans-cinnamic acid, benzylalcohol, salicylic acid, geranyl pyrophosphate, farnesyl pyrophosphate, jasmonic acid, eugenol or isoeugenol.

49. The method of claim 46 wherein the floral scent precursor is present in the composition in the amount of from about 1 ppm to about 1000 ppm.

50. The method of claim 46 wherein the composition further comprises preservatives, excipients or additives.

51. The method of claim 46 wherein the nutrient source is a carbohydrate.

52. The method of claim 51 wherein the carbohydrate is sucrose, fructose, glucose, galactose or raffinose.

53. The method of claim 46 wherein the nutrient source is present in the amount of about 0.5% to about 10% by weight of the composition.

54. A method for increasing the floral scent emission from a plant in order to facilitate the identification of at least one volatile compound from said plant, the method comprising the step of:
applying to a plant an effective amount of a composition comprising at least one floral scent precursor and a nutrient source, wherein the floral scent precursor increases the emission of a floral scent from a plant by inducing or activating floral scent biosynthesis and/or emission, wherein the increased emission of said floral scent from the plant is sufficient to facilitate the identification of at least one volatile compound from said plant.

55. The method of claim 54 wherein the floral scent precursor is benzoic acid, trans-cinnamic acid, benzylalcohol, salicylic acid, geranyl pyrophosphate, farnesyl pyrophosphate, jasmonic acid, eugenol or isoeugenol.

56. The method of claim 54 wherein the floral scent precursor is present in the composition in the amount of from about 1 ppm to about 1000 ppm.

57. The method of claim 54 wherein the composition further comprises preservatives, excipients or additives.

* * * * *